United States Patent [19]

Anderson, Jr. et al.

[11] Patent Number: 5,759,405
[45] Date of Patent: Jun. 2, 1998

[54] APPARATUSES AND METHODS FOR ELECTROCHEMICALLY MODIFYING THE RETENTION OF SPECIES ON CHROMATOGRAPHY MATERIAL

[75] Inventors: James M. Anderson, Jr., Arlington Heights; Raaidah Saari-Nordhaus, Lindenhurst, both of Ill.; Carl W. Sims, St. Paul; Yuri E. Gerner, Mendota Heights, both of Minn.

[73] Assignee: Alltech Associates, Inc., Deerfield, Ill.

[21] Appl. No.: 911,847

[22] Filed: Aug. 15, 1997

Related U.S. Application Data

[63] Continuation of Ser. No. 486,210, Jun. 7, 1995, abandoned, which is a continuation-in-part of Ser. No. 399,706, Mar. 3, 1995, abandoned.

[51] Int. Cl.$^6$ .................................................. B01D 15/08
[52] U.S. Cl. ........................ 210/656; 210/198.2; 210/670; 210/748; 73/61.52; 73/61.53; 73/61.58
[58] Field of Search ........................... 210/656, 748, 210/198.2, 670; 73/61.52, 61.53, 61.58

[56] References Cited

U.S. PATENT DOCUMENTS

| | | | |
|---|---|---|---|
| 2,980,598 | 4/1961 | Stoddard | 205/688 |
| 3,557,532 | 1/1971 | Broerman | 210/656 |
| 3,594,294 | 7/1971 | Pretorius et al. | 210/656 |
| 3,640,813 | 2/1972 | Nerenberg | 204/615 |
| 3,694,335 | 9/1972 | Pretorius et al. | 205/687 |
| 3,722,181 | 3/1973 | Kirkland et al. | 95/88 |
| 3,795,313 | 3/1974 | Kirkland et al. | 210/198.2 |
| 3,897,213 | 7/1975 | Stevens et al. | 422/81 |
| 3,918,906 | 11/1975 | Small et al. | 436/161 |
| 3,920,397 | 11/1975 | Small et al. | 436/79 |
| 3,925,019 | 12/1975 | Small Hamish et al. | 436/79 |
| 3,926,559 | 12/1975 | Stevens | 436/79 |
| 4,242,097 | 12/1980 | Rich, Jr. et al. | 436/100 |
| 4,265,634 | 5/1981 | Pohl | 436/161 |
| 4,314,823 | 2/1982 | Rich, Jr. et al. | 436/100 |
| 4,403,039 | 9/1983 | Ban et al. | 436/150 |
| 4,404,065 | 9/1983 | Matson | 205/780.5 |
| 4,413,505 | 11/1983 | Matson | 73/61.55 |
| 4,455,233 | 6/1984 | Pohl et al. | 210/635 |
| 4,459,357 | 7/1984 | Jansen et al. | 204/520 |
| 4,474,664 | 10/1984 | Stevens et al. | 210/656 |
| 4,486,312 | 12/1984 | Slingsby et al. | 210/656 |
| 4,511,659 | 4/1985 | Matson | 205/780.5 |
| 4,584,075 | 4/1986 | Goldstein et al. | 204/522 |
| 4,594,135 | 6/1986 | Goldstein et al. | 204/551 |
| 4,632,745 | 12/1986 | Giuffrida et al. | 204/632 |
| 4,643,814 | 2/1987 | Goldstein et al. | 204/551 |
| 4,672,042 | 6/1987 | Ross, Jr. et al. | 436/161 |

(List continued on next page.)

FOREIGN PATENT DOCUMENTS

| | | |
|---|---|---|
| 52-31958 | 3/1977 | Japan . |
| 53-116278 | 11/1978 | Japan . |
| 60-207055 | 3/1984 | Japan . |
| 59-133459 | 7/1984 | Japan . |

OTHER PUBLICATIONS

G. I. Mal'tsev et al., "Investigation of Ion Exchange on KU-2 Cationite on Application of an Audio-Frequency Alternating Electrical Field", 3 pages (1971) No month available.

(List continued on next page.)

*Primary Examiner*—Bruce F. Bell
*Assistant Examiner*—John S. Starsiak, Jr.
*Attorney, Agent, or Firm*—Brinks Hofer Gilson & Lione

[57] ABSTRACT

An apparatus and method for electrochemically modifying the retention of a species on a chromatography material is disclosed. The apparatus comprises a housing having an effluent flow channel adapted to permit fluid flow therethrough. The effluent flow channel comprises chromatography material. The apparatus further comprises first and second electrodes positioned such that at least a portion of the chromatography material is disposed between the first and second electrodes, and fluid flow through the apparatus is between, and in contact with, the first and second electrodes.

23 Claims, 13 Drawing Sheets

U.S. PATENT DOCUMENTS

| | | | |
|---|---|---|---|
| 4,732,686 | 3/1988 | Small et al. | 210/656 |
| 4,747,929 | 5/1988 | Siu et al. | 204/632 |
| 4,751,004 | 6/1988 | Stevens et al. | 210/659 |
| 4,751,189 | 6/1988 | Rocklin | 436/150 |
| 4,861,555 | 8/1989 | Mowery, Jr. | 422/70 |
| 4,925,541 | 5/1990 | Giuffrida et al. | 204/524 |
| 4,952,126 | 8/1990 | Hanaoka et al. | 422/70 |
| 4,981,804 | 1/1991 | Hanaoka et al. | 436/150 |
| 4,999,098 | 3/1991 | Pohl et al. | 210/670 |
| 5,032,265 | 7/1991 | Jha et al. | 210/195.2 |
| 5,045,204 | 9/1991 | Dasgupta et al. | 210/635 |
| 5,062,961 | 11/1991 | Doury-Berthod et al. | 210/656 |
| 5,068,090 | 11/1991 | Connolly | 422/82.02 |
| 5,132,018 | 7/1992 | Jones et al. | 210/656 |
| 5,149,661 | 9/1992 | Gjerde et al. | 436/178 |
| 5,248,426 | 9/1993 | Stillian et al. | 210/635 |
| 5,352,360 | 10/1994 | Stillian et al. | 210/198.2 |
| 5,423,965 | 6/1995 | Kunz | 205/702 |
| 5,518,622 | 5/1996 | Stillian et al. | 210/635 |
| 5,633,171 | 5/1997 | Small et al. | 436/161 |

OTHER PUBLICATIONS

Z. W. Tian et al., "High-Performance Electrochemical Suppressor For Ion Chromatography", *Journal of Chromatography*, vol. 439, pp. 159–163 (1988) No month available.

D. L. Strong et al., "Electrodialytic Membrane Suppressor for Ion Chromatography", *Analytical Chemistry*, vol. 61, pp. 939–945 (1989) no month available.

D. T. Gjerde et al., "Suspension Postcolumn Reaction Detection Method for Liquid Chromatography", *Analytical Chemistry*, vol. 62, pp. 612–614 (1990) No month available.

A. Henshall et al., "A Recent Development in Ion Chromatography Detection: The Self-Regenerating Suppressor" (1992) No month available.

Brochure of Applicants' assignee entitled "Improve the Performance of Any Ion Chromatograph", 4 pages, Bulletin #284, Alltech Associates, Inc. (1993) No month available.

S. Rabin et al., "New Membrane-Based Electrolytic Suppressor Device for Suppressed Conductivity Detection in Ion Chromatography", *Journal of Chromatorgraphy*, vol. 640, pp. 97–109 (1993) No month available.

R. S. Nordhaus et al., "Ion Chromatographic Analysis of Anions using a Solid-Phase Chemical Suppressor", 9 pages, Reprinted from *American Laboratory* (1994) No month available.

Brochure entitled "Microparticulate Chemical Suppression with Sarasep Micro Ion Chromatography", 1 page No date available.

Brochure of DionexJ entitled "Self-Regenerating Suppressor (SRS)"No date available.

"Ion Chromatography", Hamish Small, Plenum Press No date available.

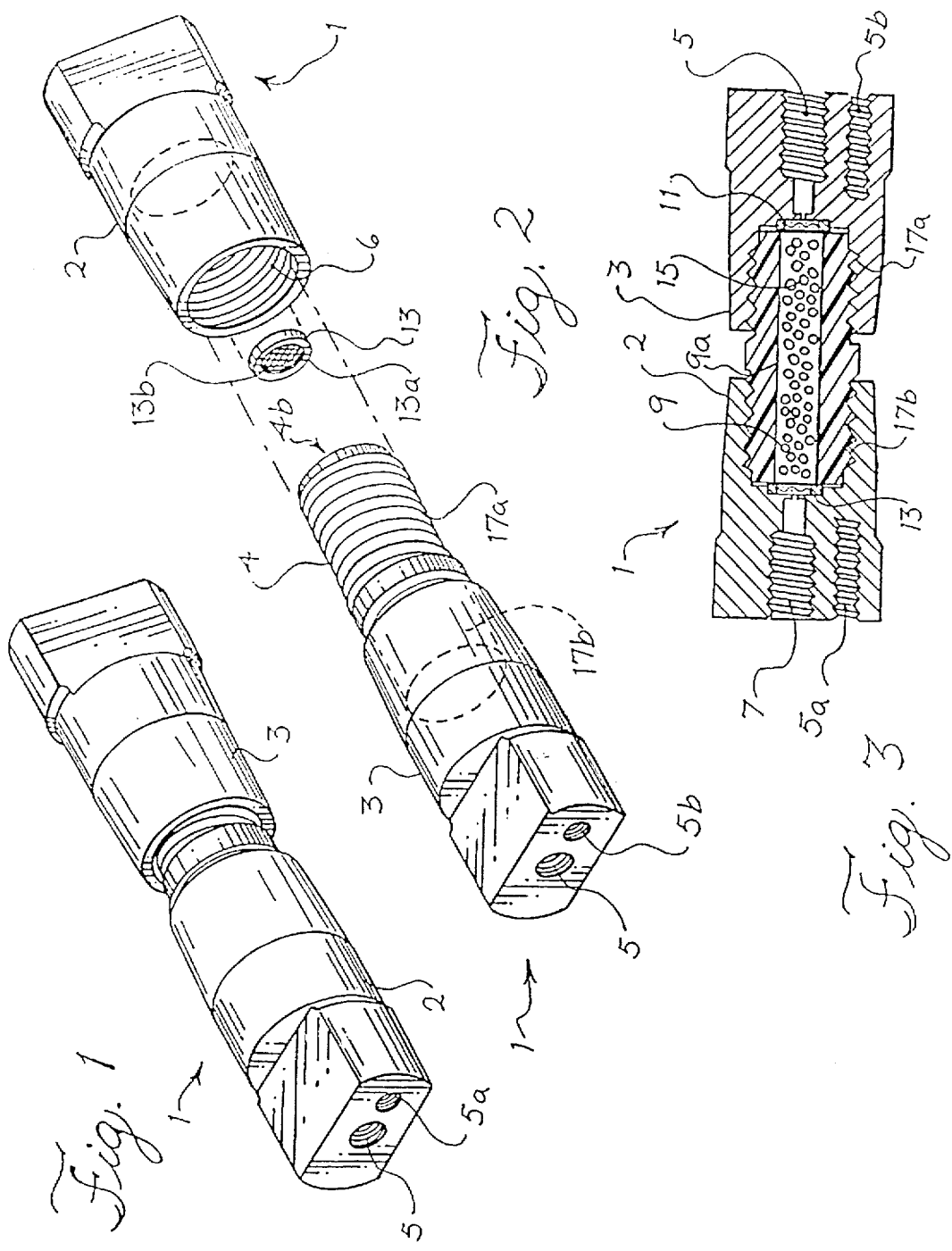

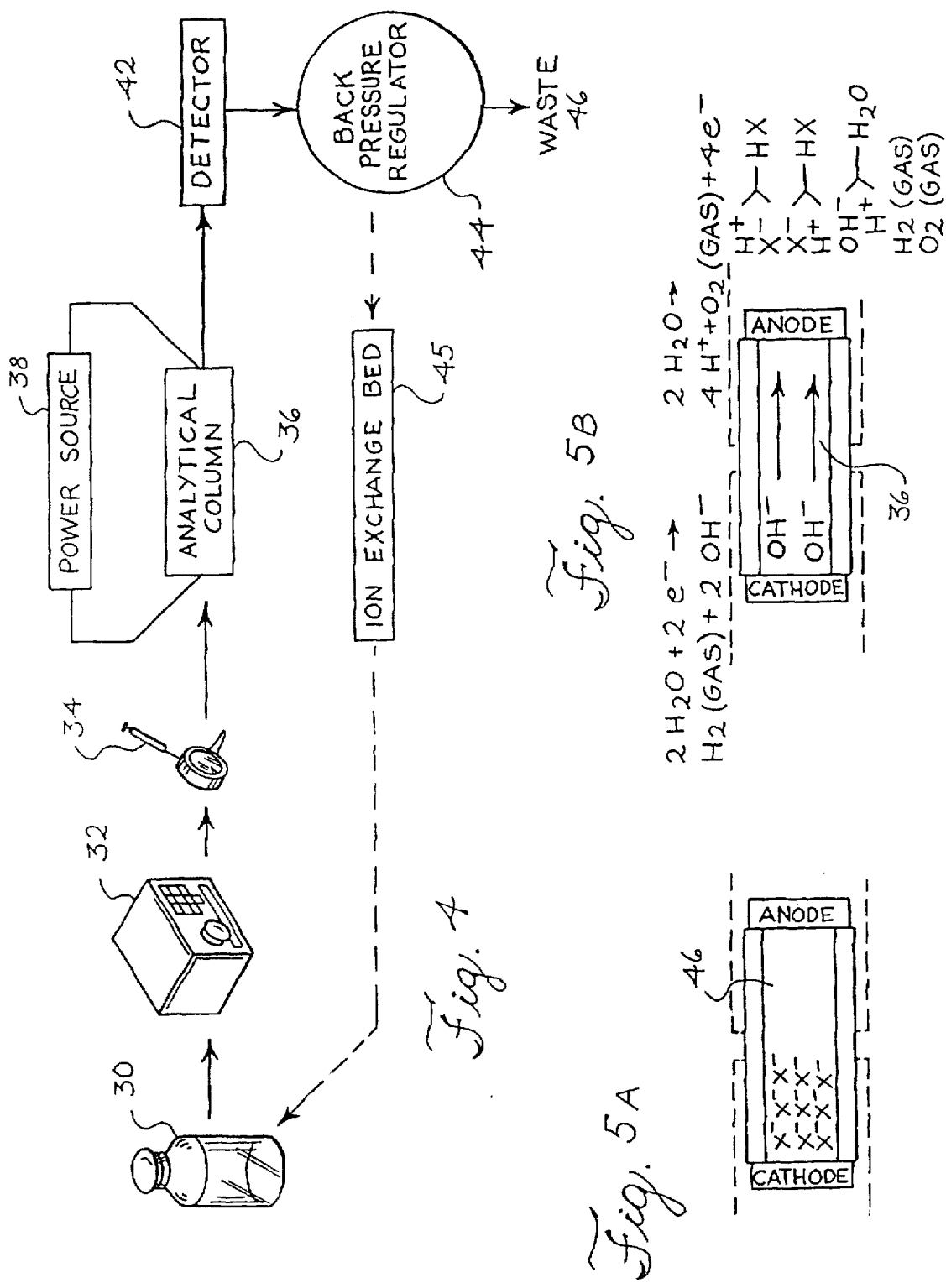

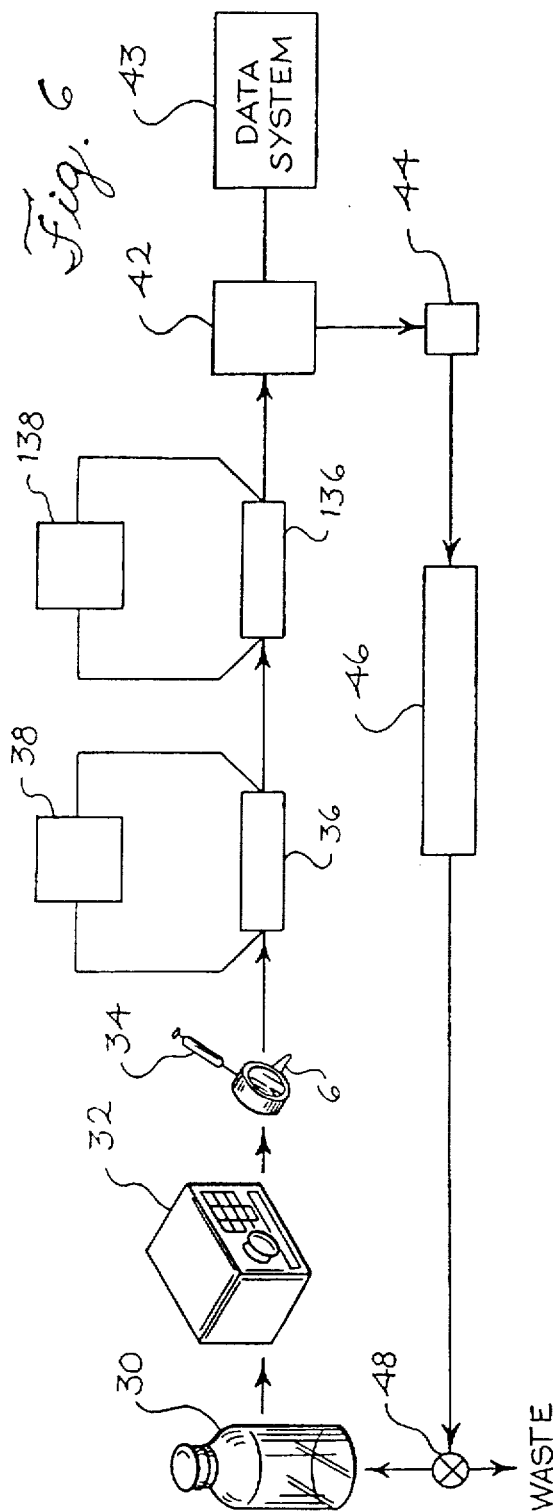
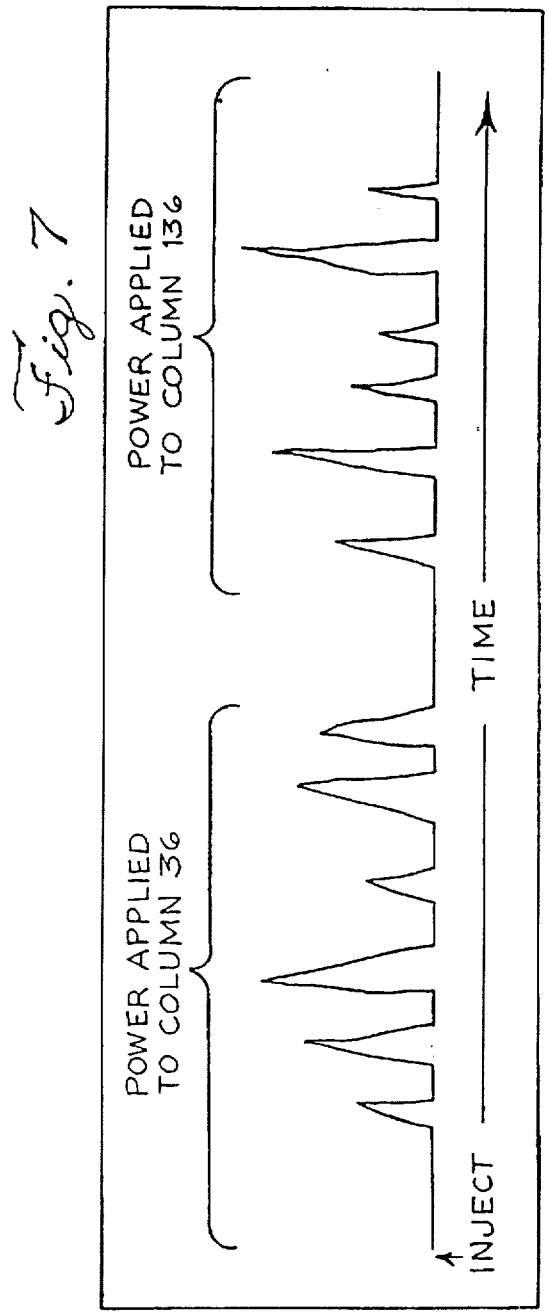

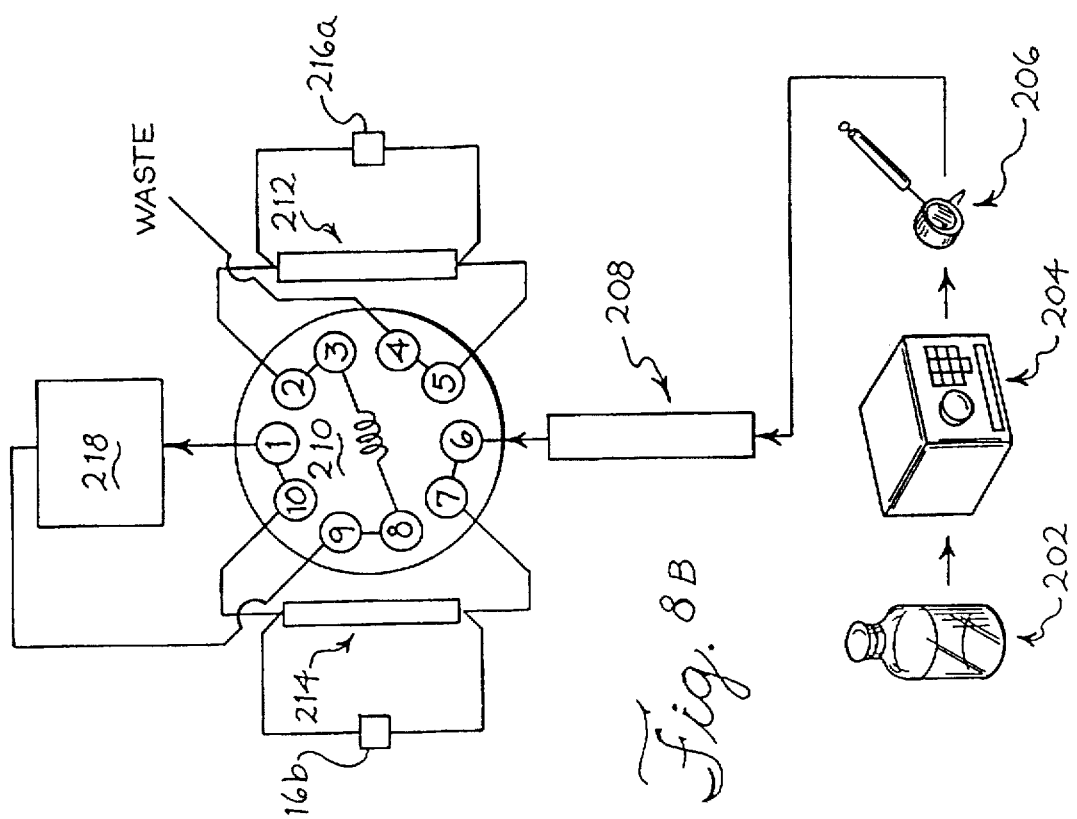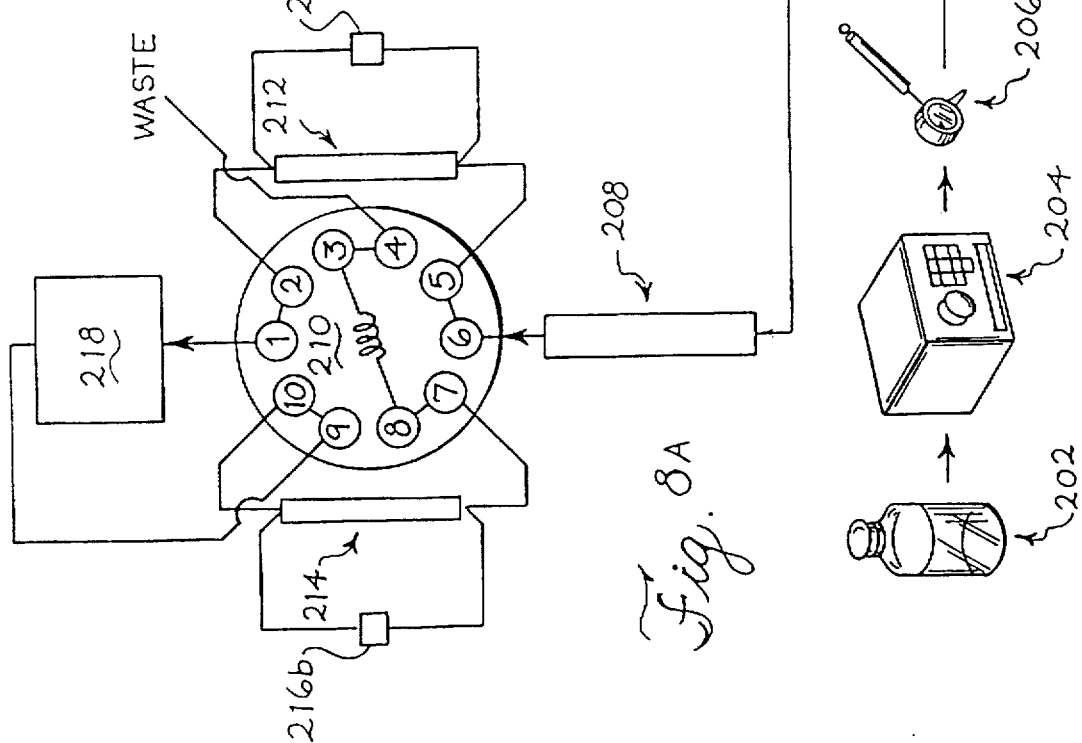

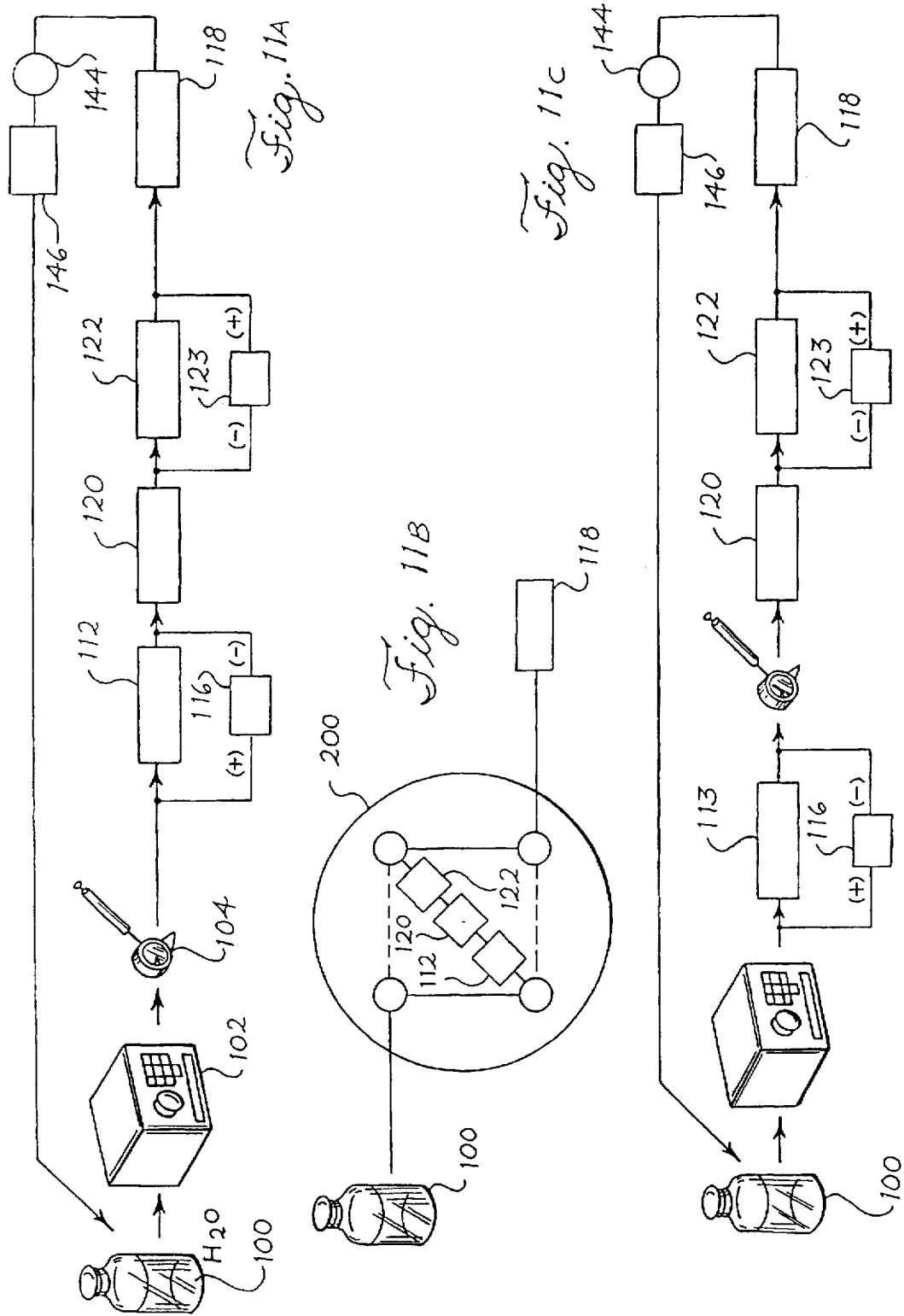

APPARATUSES AND METHODS FOR ELECTROCHEMICALLY MODIFYING THE RETENTION OF SPECIES ON CHROMATOGRAPHY MATERIAL

This application is a continuation of application Ser. No. 08/486,210, filed Jun. 7, 1995, now abandoned, which is a continuation-in-part of application Ser. No. 08/399,706, filed Mar. 3, 1995 now abandoned.

FIELD OF THE INVENTION

This intention relates to chromatography columns, apparatuses, and methods. In particular, the columns of the present invention can be used as the separation column in electroelution chromatography and are also adaptable for use as a self-regenerating suppressor in suppressed ion chromatography. The columns of the present invention may also be used to separate a wide range of compounds on both an analytical and preparative scale.

BACKGROUND OF THE INVENTION

A. Single Column Ion Chromatography

Single Column Ion Chromatography (SCIC) is a method of ion analysis in which ions are separated in an ion exchange column (e.g., separator column) and subsequently measured by a conductivity detector connected directly to the separator column. In SCIC, special ion exchange resins of low capacity, and eluants with either much higher or much lower equivalent conductance than the ions being measured must be employed. In ion chromatography, sample ions generate a signal at a conductivity detector. The signal is proportional to the sample ion concentration and is the difference in equivalent conductance between the sample ion and the eluant ion. SCIC sensitivity is limited by the difference in equivalent conductance between the sample ions and the eluant ions. This sensitivity is adequate and even preferred for some sample types, especially for cationic samples, where the difference in equivalent conductance between the sample and eluant ions is very large. However, for many other samples, particularly anionic samples, where the difference in equivalent conductance between the sample ions and eluant ions is small, sensitivity can be greatly increased by a second and preferred type of ion analysis called chemically suppressed ion chromatography (SIC).

B. Suppressed Ion Chromatography (SIC)

Suppressed ion chromatography (SIC) is a form of commonly practiced ion analysis characterized by the use of two ion-exchange columns in series followed by a flow through conductivity detector. The first column, called the separation column, separates the ions of an injected sample by elution of the sample through the column using an electrolyte as an eluant, i.e., usually dilute base or acid in deionized water. The second column, called the "suppressor" or "stripper", serves two purposes. First, it lowers the background conductance of the eluant to reduce noise. Second, it enhances the overall conductance of the sample ions. The combination of these two factors significantly enhances the signal to noise ratio, thus increasing sensitivity.

This technique is described in more detail in U.S. Pat. Nos. 3,897,213, 3,920,397, 3,925,019 and 3,926,559. In addition, suitable ion exchange packings for the separation column are described in detail in U.S. Pat. Nos. 3,966,596, 4,101,460 and 4,119,580. A detailed description of ion chromatography is additionally provided in Small et al., "Proceedings of an International Conference on the Theory and Practice of Ion Exchange," University of Cambridge, U.K., July, 1976; and also, Small et al., "Novel Ion Exchange Chromatographic Method Using Conductimetric Detection", Analytical Chemistry, Vol. 47, No. 11, September 1975, pp. 1801 et seq. The foregoing patents and literature publications are fully incorporated herein by reference.

C. Gradient Elution Technology

To separate or eluant sample ions retained on an ion-exchange column, an eluant containing co-ions of the same charge of the sample ions is routed through the separation column. The sample co-ions in the eluant partially displace the sample ions on the ion-exchange column, which cause the displaced sample ions to flow down the column along with the eluant. Typically, a dilute acid or base solution in deionized water is used as the eluant. The eluant is typically prepared in advance and routed through the column by either gravity or a pump.

Rather than using a homogenous eluant throughout the separation process, it is sometimes advantageous to use a gradient eluant, i.e., an eluant wherein the concentration of one or more components changes with time. Typically, the eluant starts at a weak eluting strength (e.g. a low concentration of the sample co-ions) and gets stronger (e.g. a higher concentration of the sample co-ions) during the separation process. In this way, easily eluted ions are separated during the weaker portion of the gradient, and ions that are more difficult to elute are separated during the stronger portion of the gradient. The eluant concentration changes during the gradient and suppressing or balancing the concurrent change in background conductance is required so the sample signal may be discriminated from the background signal. An example of such gradient elution techniques are disclosed in U.S. Pat. Nos. 4,751,189 and 5,132,018, the entire disclosures of which are incorporated herein by reference.

While the above patents utilize solutions prepared in advance to form a gradient eluant, U.S. Pat. No. 5,045,204 to Dasgupta et al. uses electrochemical methods to generate a high purity eluant stream that may flow directly to the separation column as it is produced, and which may be generated as a gradient. In the Dasgupta patent, a product channel is defined by two permselective membranes and is fed by a source of purified water. One of the permselective membranes only allows the passage of negatively charged hydroxide ions, which are generated on the side of this membrane opposite the product channel by the electrolysis of water at a cathode. The hydroxide ions are driven by an electric field through the membrane into the product channel in an amount corresponding to the strength of the electric field. The other permselective membrane only allows the passage of positively charged ions. On the side of this membrane opposite the product channel there is a source channel, which is continuously fed with a NaOH solution and in which an anode is positioned. The $Na^+$ ions are driven by the electric field through the membrane into the product channel in an amount corresponding to the strength of the electric field. By this process, a high purity sodium hydroxide (NaOH) solution is produced. This solution may be used as the eluant for a chromatography column, and the concentration of this eluant may be varied during the chromatographic separation by varying the strength of the electric field, thereby generating a gradient eluant.

The foregoing methods of elution ion chromatography suffer from certain disadvantages, however. Among these disadvantages is that an outside source of eluant or eluant counter-ions is required. Also, after eluting the sample ions from the chromatography column, all of these eluants require suppression in order to provide an accurate quantitative analysis of the sample ions. Finally, in general practice, all of the above methods of eluting are only applicable to one of either cation or anion sample ions within a single sample run. If one wishes to analyze both the cations and anions from a single sample, two chromatographic separations must be performed using either two apparatuses and two distinct eluants, or a single instrument with two or more columns and complex switching valves.

D. Prior Suppressor Technology

Chemical suppression for IC serves two purposes. First, it lowers the background conductance of the eluant to reduce baseline noise. Second, it enhances the overall conductance of the sample ions to increase the signal. The combination of these two factors significantly enhances the signal-to-noise ratio, and increase the detectivity of the sample ions. For example, in anion analysis, two ion-exchange reactions take place in a suppressor column when the eluant comprises sodium hydroxide and the ion exchange packing material in the suppressor column comprises exchangeable hydronium ions:

1) Eluant:

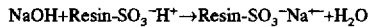

2) Analyte:

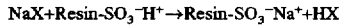

where X=anions ($Cl^-$, $NO_2^-$, $Br^-$, etc.)

The relatively high conductivity sodium hydroxide eluant is converted to the relatively low conductivity water when the sodium ions from the eluant displace the hydronium ions on the ion exchange packing material in the suppressor. The sample anions are converted from their salt form into their more conductive acid form by exchanging their counter-ions for hydronium ions in the suppressor. The eluant is preferably a solution of any salt that forms a weakly conductive acid after going through the suppressor. Examples of such eluants in anion analysis include sodium hydroxide, sodium carbonate, or sodium tetraborate solutions.

Various suppressor devices that operate on the above principles have been used for IC. These include:

1. Packed-Bed Suppressors

Packed-Bed Suppressors were introduced in about 1973 (see, for example, U.S. Pat. Nos. 3,918,906, 3,925,019, 3,920,397, 3,926,559, 4,265,634, and 4,314,823, the entire disclosures of which are incorporated herein by reference). These suppressors consist of large columns containing strong acid cation-exchange resins in hydronium form (for anion analysis). In order to house enough resin, these columns are very large (i.e., 250 mm×7.8 mm). However, these columns have a large dead volume, which causes considerable peak dispersion and broadening. This, in turn, results in a loss of chromatographic efficiency. Moreover, after several hours of operation, the resin bed becomes exhausted (all the hydronium ions on the exchange sites are replaced by the sample and the eluant counterions). The suppressor column must then be taken off-line and regenerated by flushing the column with an acid to regenerate the hydronium ion exchange sites in the resin bed. The regeneration of the suppressor column, of course, is time consuming and interrupts the analysis.

Another disadvantage of these packed bed suppressors is that weakly ionized species such as organic acids can penetrate the protonated cation exchange sites and interact by inclusion within the resin bed. This causes variable retention times and peak areas as the suppressor becomes exhausted. Also, some ions can undergo chemical reactions in the suppressor. For example, nitrite has been shown to undergo oxidation in these prior art packed bed suppressors leading, to variable recovery and poor analytical precision.

2. Hollow-Fiber Membrane Suppressors

In about 1982, hollow fiber membrane suppressors were introduced (see, for example, U.S. Pat. Nos. 4,474,664 and 4,455,233, the entire disclosures of which are incorporated herein by reference). Hollow fiber membrane suppressors were designed to overcome the drawbacks of the packed bed suppressors. The hollow fiber membrane suppressors consist of a long, hollow fiber made of semi-permeable, ion-exchange material. Eluant passes through the hollow center of the fiber, while a regenerating solution bathes the outside of the fiber. Suppressor ions cross the semi-permeable membrane into the hollow center of the fiber, and suppress the eluant. The regenerating solution provides a steady source of suppressor ions, allowing continual replacement of the suppressor ions as they pass to the eluant flow channel in the hollow center of the fiber. The main advantage of the hollow fiber design is that the chromatography system can be continuously operated because there is no need to take the suppressor off-line for regeneration, as is the case with the packed bed suppressors.

However, the hollow fiber design introduced new problems. The small internal diameter of the fibers reduces the surface area available for ion exchange between eluant and the regenerant. This limits the suppression capability of the hollow fiber suppressors to low flow rates and low eluant concentrations. Additionally, because the fiber is bathed in the regenerant solution, the counterion of the suppressor ions can leak into the eluant channel, and cause higher background conductivity and baseline noise at the detector.

3. Flat-Sheet Membrane Suppressors

Flat-sheet membrane suppressors were introduced in about 1985 (see, for example, U.S. Pat. Nos. 4,751,189 and 4,999,098, the entire disclosures of which are incorporated herein by reference). In these suppressors, the ion exchange tubing in the hollow-fiber suppressor is replaced with two flat semi-permeable ion exchange membranes sandwiched in between three sets of screens. The eluant passes through a central chamber which has ion exchange membrane sheets as the upper and lower surfaces. The volume of the eluant chamber is very small, so band broadening is minimal. Since the membrane is flat, the surface area available for exchange between the sample counterions and the suppressor ions in the regenerant is greatly increased. This increases the suppression capacity allowing high flow rates, high eluant concentration, and gradient analyses. Preferably, the regenerant flows in a direction counter to the sample ions over the outer surfaces of both membranes, providing a constant supply of suppressor ions.

A major drawback, however, of membrane suppressors is that they require a constant flow of regenerant to provide continuous suppression/operation. This consumes large volumes of regenerant and produces large volumes of chemical waste, significantly increasing operating cost. An additional pump or device is required to continuously pass the regenerant through the suppressor, increasing the instrument's complexity and cost while reducing reliability. Also, organic compounds can irreversibly adsorb onto the hydrophobic ion-exchange membrane, reducing its efficiency to the point where it requires replacement (membranes are typically replaced every six months to two years). Finally, the membranes are very thin and will not tolerate much backpressure. Thus, membrane rupture is a concern anytime downstream backpressure increases due to blockages.

4. Solid Phase Chemical Suppressor (SPCS)

Alltech Inc., the assignee of the present application, developed solid phase chemical suppressors (SPCS) in about 1993, which were essentially an improved version of the original packed bed suppressors. Problems associated with the original packed bed suppressors, such as band broadening, variable retention time and peak area, and the oxidation of nitrite in the suppressor, were greatly reduced. The Alltech SPCS uses disposable cartridges containing ion exchange packing material comprising suppressor ions as the suppressor device. The inexpensive cartridges are simply discarded and replaced with a new cartridge when the suppressor ions are exhausted. Thus, no regeneration is required, thereby eliminating the need for expensive or complex systems for regenerating suppressor ions.

In Alltech's SPCS system, a 10-port switching valve and two disposable suppressor cartridges are typically employed. The effluent from the analytical column flows through one cartridge at a time. While one cartridge is being used, the suppressed detector effluent (typically water or carbonic acid) flows through the other suppressor cartridge to pre-equilibrate the cartridge. This reduces the baseline shift due to conductance change when the valve is switched to the other suppressor cartridge. When all the suppressor ions from one cartridge are replaced by the eluant and sample counterions, the valve is switched, placing the second cartridge in the active position, and the exhausted suppressor cartridge is replaced. This allows continuous operation. However, the Alltech system still requires someone to switch the valve manually when the first cartridge is exhausted. Each cartridge typically provides between 6 to 9 hours of operation, and thus fully unattended or overnight operation might not be possible in certain applications with the Alltech SPCS system.

5. Electrochemical Suppression

Electrochemical suppressors were introduced in about 1993. These suppressors combine electrodialysis and electrolysis in a flat-sheet membrane suppressor column similar to those described under heading section 3 above (see U.S. Pat. Nos. 4,459,357 and 5,248,426, the entire disclosures of which are incorporated herein by reference).

For example, U.S. Pat. No. 5,248,426 to Stillian et al. discloses a suppressor which contains a central chromatography effluent flow channel bordered on both sides by ion exchange membranes with exchangeable ions of the opposite charge of the sample ions. On the side of each membrane opposite the effluent flow channel are first and second detector effluent flow channels. The sample ions and eluant are routed through the chromatography effluent flow channel, and the water-containing detector effluent is routed through the detector effluent flow channels in the suppressor. An electrode is positioned in both of the detector effluent flow channels.

By energizing the electrodes, an electrical potential is generated in the suppressor transverse to the liquid flow through the chromatography flow channel. When the water-containing detector effluent contacts the energized electrodes, it undergoes electrolysis. In anion analysis for example, the suppressor hydronium ions generated at the anode in a first detector-effluent channel are transported across the ion exchange membrane into the chromatography effluent flow channel, where they combine with the sample anions to form the highly conductive acids of the sample anions. The suppressor hydronium ions also combine with the hydroxide ions in the eluant (in anion analysis) to convert the eluant into the relatively non-conductive water. At the same time, the eluant and sample counterions are transported from the chromatography effluent channel across the ion exchange membrane into a second detector effluent flow channel where they combine with the hydroxide ions generated by the electrolysis of the water-containing detector effluent at the cathode in the second detector effluent flow channel. The resulting bases of the eluant counterions are then routed to waste.

Thus, the electric field generated in the suppressor column disclosed in Stillian et al. simultaneously generates suppressor ions and promotes ion-flow between the electrodes in a direction transverse to the fluid flow through the suppressor. The mass transport of ions is across a first ion exchange membrane from a first detector effluent flow channel to the chromatography effluent flow channel, and across a second ion exchange membrane to a second detector effluent flow channel.

Although the electrochemical suppressor device disclosed in Stillian et al. offers certain advantages (i.e. no separate regenerant source is required), it still suffers from certain disadvantages. Irreversible adsorption of organic components and membrane breakage under pressure may still occur in the apparatus and method disclosed in Stillian. Also, the method of electrochemical suppression disclosed in Stillian can only be used to analyze solely anions or solely cations in any one sample. Finally, the Stillian method does not work well with electroactive eluants or organic solvents. Electroactive eluants, such as hydrochloric acid, commonly employed as an eluant for cation analysis, undergo electrochemical reaction in the suppressor producing by-products that damage the membrane. Also, certain organic eluant components such as methanol undergo electrochemical reaction in the electrochemical suppressor producing by-products that are conductive and which interfere with the detection of sample ions. Such electroactive eluant systems may not be effectively employed in the Stillian method.

The column, apparatuses, and methods of the present invention reduce or avoid many of the foregoing problems.

SUMMARY OF THE INVENTION

In one aspect of the present invention, the foregoing disadvantages are overcome. The column of the present invention can be used in apparatuses and methods for generating an eluant in-situ that does not require an outside source of sodium or other electrolytes. Additionally, the column of the present invention can be used in apparatuses and methods that generate a self-suppressing eluant and, therefore, a second suppressor column is not required. Moreover, the column of the present invention can be adapted for use in apparatuses and methods for analyzing both cations and anions in a single sample run.

In one embodiment of the present invention, a housing is provided. The housing has an effluent flow channel adapted to permit fluid flow through the housing. The housing further contains chromatography packing material disposed in the effluent flow channel. The housing also contains first and second electrodes which are positioned such that at least a portion of the chromatography packing material is disposed between the first and second electrodes, and fluid flow through the housing is from one of the first or second electrodes to the other.

In another aspect of the invention, an apparatus for electrochemically modifying the retention of a species on chromatography material is provided. The apparatus has a housing, which comprises an effluent flow channel. The effluent flow channel comprises chromatography material, and the effluent flow channel is adapted to permit fluid flow therethrough. The apparatus further comprises a first electrode and a second electrode. These first and second electrodes are positioned such that at least a portion of the chromatography material is disposed between the first and second electrodes, and the fluid flow through the effluent flow channel is between, and in contact with, the first and second electrodes. Also, the apparatus further comprises a power source connected to the first and second electrodes.

In yet another aspect of the invention, a method of electrochemically modifying the retention of a compound or species on a chromatography material is provided. According to this method, an effluent flow channel is provided comprising a stationary phase containing chromatography material on which the compound or species is retained. A first and a second electrode are also provided, and the electrodes are positioned such that at least a portion of the chromatography material is disposed between the first and second electrodes. A mobile phase comprising an eluant is further provided. The eluant is flowed between, and in contact with, the first and second electrodes thereby electrochemically modifying the eluant. The modified eluant is flowed to the chromatography material, which modifies the retention of the compound or species on the chromatography material.

The foregoing housing and apparatus may be used as a chromatography column, a self-regenerating suppressor, and in various chromatography apparatuses according to various embodiments of the present invention. The apparatus of the present invention may also be used in various methods of separating ions, proteins, and other compounds. The apparatus of this invention may also be used in methods of generating a high purity eluant, and for generating a gradient in gradient elution chromatography.

These and other advantages of the invention, as well as the invention itself, will be best understood with reference to the attached drawings, a brief description of which follows, along with the detailed description of the invention provided herein.

BRIEF DESCRIPTION OF THE DRAWINGS

FIG. 1 is a perspective view of a preferred column of the present invention.

FIG. 2 is an exploded view of the column illustrated in FIG. 1.

FIG. 3 is a cross-sectional view of the column illustrated in FIG. 1.

FIG. 4 is a schematic view of a chromatography apparatus for use in a method of electroelution chromatography.

FIGS. 5A and 5B are schematic views of the chromatography column of FIG. 1 showing ion exchange when the column is used in a method of electroelution chromatography.

FIG. 6 is a schematic view of a chromatography apparatus for use in a method of electroelution chromatography.

FIG. 7 is an illustrative chromatogram using the chromatography apparatus depicted in FIG. 6 in a method of electroelution chromatography where anions and cations in the same sample are detected.

FIGS. 8A–8D are schematic views of chromatography apparatuses where the column of FIG. 1 is used as a solid phase chemical suppressor.

FIGS. 11A and 11B are schematic views of a chromatography apparatus where two columns of the present invention are used as an eluant generating column to generate a high purity eluant, and as a solid phase chemical suppressor, respectively.

FIG. 11C is a schematic view of a chromatography apparatus where the column of FIG. 1 is used as a solid phase chemical suppressor.

DETAILED DESCRIPTION OF THE DRAWINGS AND PRESENTLY PREFERRED EMBODIMENTS

Figure 8D:
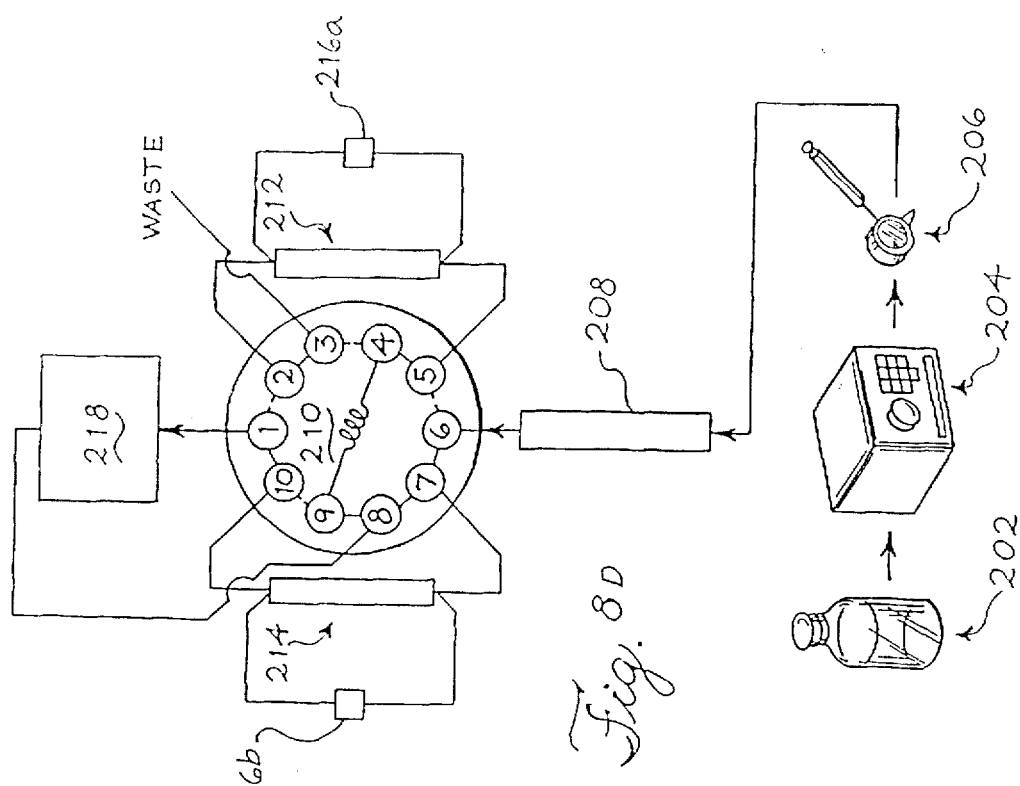

The preferred column of the present invention is especially adapted for use in chromatography apparatuses and methods. With reference to FIGS. 1–3, the preferred chromatography column comprises a housing 1. The housing 1 consists of female end fitting 2 and male end fitting 3. The female end fitting and the portion of the male end fitting other than arm 4 are preferably made from a conductive material. Preferably, these pieces are made from titanium or stainless steel coated with inert material. The male end fitting, 3 has a threaded arm 4 secured thereto. The arm 4 of the male end fitting 3 further comprises a cavity 4b. The threaded arm is preferably made from a non-conductive, water proof plastic material. The arm 4 of male end fitting 3 is most preferably made from polyetheretherketone (PEEK). The female end fitting 2 also has a cavity 6. The cavity 6 is preferably threaded and adapted to receive the threaded arm 4 of male end fitting 3.

Housing 1 is easily assembled by releasably securing arm 4 of male end fitting 3 in the cavity 6 of the female end fitting 2. This is accomplished by simply screwing the threaded arm 4 of the male end fitting 3 into the cavity 6 of female end fitting 2. Similarly, the housing 1 may be just as easily dismantled by unscrewing the threaded arm 4 of male end fitting 3 from the cavity 6 of female end fitting 2. When the housing 1 is assembled, the cavity 4b of the arm 4 of male end fitting 3 provides part of an effluent flow channel 9, which is adapted to permit fluid flow through the housing 1.

The male end fitting 3 has an opening 5, which is adapted to permit fluid to enter or exit the housing 1. The female end fitting 2 also has an opening 7 which is adapted to permit fluid to enter or exit the housing 1. Preferably, openings 5 and 7 are threaded for easy connection to fluid lines in the chromatography apparatuses and methods described herein. Extending from the opening 5 of male end fitting 3 to opening 7 of female end fitting 3 when the housing 1 is assembled is the effluent flow channel 9.

The housing 1 further preferably comprises first and second electrodes 11 and 13. Preferably, first and second electrodes 11 and 13, respectively, are positioned at opposite ends of the effluent flow channel 9, and are positioned such that the fluid flow through the housing 1 is from one of the first or second electrodes to the other. In the most preferred embodiment, the electrodes 11 and 13 are positioned near the openings 5 and 7 of the male end fitting 3 and female 2 end fitting, respectively, of the housing 1.

The housing 1 further comprises chromatography packing material 15 disposed within the effluent flow channel 9. The chromatography packing material 15 is selected as discussed with respect to the various embodiments discussed below. Preferably, at least a portion of the chromatography packing material is disposed between the first and second electrodes. However, in an alternative embodiment of the present invention, those skilled in the art will appreciate that, instead of using chromatography packing material 15, the effluent flow channel 9 may be defined by chromatography material (not shown). For example, chromatography material (not shown) may be coated on the wall 9a of the effluent flow channel 9.

Alternatively, the wall 9a of effluent flow channel 9 may comprise chromatography material such as a hollow tubing containing chromatography stationary phases (not shown). One such material suitable for use in this alternate embodiment is Nafion® available from Perma Pure, Toms River, N.J. In view of the foregoing, those in the art will appreciate, the term "chromatography material" as used herein is meant to include chromatography packing material 15 (such as those materials discussed herein), coatings of chromatography material containing chromatography stationary phases (not shown) coated on the wall 9a proximate to the effluent flow channel 9, hollow tubing containing chromatography stationary phases, as well as other stationary phases commonly used in chromatography.

In a preferred embodiment, the electrodes 11 and 13 are flow-through electrodes. By flow-through electrodes, it is meant that the electrodes allow the sample ions and eluant to flow therethrough. The electrodes are preferably made from carbon, platinum, titanium, stainless steel or any other suitable conductive, non-rusting material. The preferred flow-through electrodes are sufficiently porous to allow the sample ions and eluant to flow therethrough, but sufficiently non-porous to physically retain the packing material 15 disposed in the effluent flow channel 9. The most preferred electrodes are made of platinum coated titanium, ruthenium oxide coated titanium, titanium nitride coated titanium, gold, or rhodium with an average pore size of between 0.1 μm and 100 μm.

The electrodes 11 and 13 are connected to an electrical power source (not shown) via a spade lug (not shown) which is secured in lug receptacles 5a and 5b of female end fitting 2 and male end fitting 3, respectively, by a screw or some other similar means. When the power source (not shown) is turned on, an electric current, caused by ion transport, is established from one of the first or second electrodes to the other across the chromatography packing material 15 when the column is in use. Preferably, the electric current follows along a path that is parallel to fluid flow through the column. Most preferably, the current is a constant current.

As described more fully below, the foregoing column can be used in various apparatuses and methods of electroelution chromatography. The column of the present invention may also be advantageously used as a self-regenerating, chemical suppressor. In addition, the column of the present invention can be used in a variety of other applications as well, which are also described herein.

A. Electroelution Elution Chromatography

FIGS. 4–6 illustrate the preferred column of the present invention especially adapted for use in preferred apparatuses and methods for separating, detecting, and analyzing sample ions by electroelution chromatography. As used herein, the term "electroelution chromatography" means eluting sample components from a chromatographic column by electrochemically generating or modifying the mobile phase. In other words, the mobile phase is generated or modified within or prior to entering the column by electrochemical action on the eluant.

FIG. 4 is a schematic view of an apparatus for ion analysis by electroelution chromatography using the preferred column of the present invention. The present embodiment is discussed with respect to the detection of anions in a sample. However, as discussed below, this embodiment may be modified for cation analysis, or for the analysis of anions and cations in the same test sample.

A water-containing eluant source 30 (preferably deionized water) is introduced through a high pressure liquid chromatography (HPLC) pump 32. As those skilled in the art will appreciate, a variety of pumps may be used in this embodiment. However, a metal-free, reciprocating piston pump is preferred, such as the ALLTECH Model 325 pump. The test sample, which contains anions to be detected, is injected through an injector 34, and is routed by the eluant to column 36, which is preferably constructed as depicted in FIGS. 1–3. Again, as those skilled in the art will appreciate, a variety of injectors may be used in the present embodiment. However, metal-free, rotary 6-port injection valves are preferred, such as those available from RHEODYNE (Model No. 9125) or VALCO. The column 36 comprises chromatography packing material. For anion analysis, the column 36 is packed with an anion exchange packing material (not shown). The anion exchange packing material preferably comprises exchangeable hydroxide ions. By "exchangeable," it is meant that the hydroxide ions on the packing material may be displaced (or exchanged with) the sample anions. Suitable anion exchange packing materials comprise particles of primary, secondary, tertiary, or quaternary amino functionalities, either organic or inorganic. Preferred anion exchange packing materials comprise quaternary amino functionality organic or inorganic particles. These anion exchange particles may be packed in the column in either resin form or impregnated in a membrane. Preferably, the anion exchange packing material is in resin form.

The sample anions and eluant are routed through column 36. In column 36, the sample anions displace the exchangeable hydroxide ions on the anion exchange packing material, and are retained in the column 36. Either just before or after the sample anions are retained in column 36, an electric current is generated in column 36 by turning on electrical power supply 38. As those skilled in the art will appreciate, a variety of electrical power supplies may suitably be used in the present embodiment. All that is required for the electrical power supply is that it be capable of providing from about 5–5,000 volts, more preferably from about 28–2,800 volts, and most preferably about 10–1,000 volts to the electrodes in the methods of electroelution chromatography described herein. However, a time-programmable constant-current DC power supply is preferred, such as the LABCONCO Model 3000 Electrophoresis Power Supply. Preferably, the cathode (not shown) of column 36 is located at an upstream end of the column 36, and the anode (not shown) is located at a downstream end of the column 36. Preferably, the electrodes are positioned in the effluent flow channel (not shown) of the column 36. When the water in the eluant contacts the cathode (which is the electrode located at the upstream end of the column 36 for anion analysis), it undergoes electrolysis, and hydroxide ions are generated according to the following reaction:

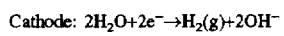

Cathode: $2H_2O + 2e^- \rightarrow H_2(g) + 2OH^-$

Similarly, when the water in the eluant contacts the anode (which is the electrode located at the downstream end of the column 36 for anion analysis), it undergoes electrolysis, and hydronium ions are generated according to the following reaction:

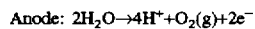

Anode: $2H_2O \rightarrow 4H^+ + O_2(g) + 2e^-$

Thus, hydroxide ions and oxygen gas are generated at the upstream end of the column 36, and are routed through the column 36. The hydroxide ions displace the retained sample anions on the anion exchange resin in column 36. The anion exchange resin is thus simultaneously regenerated back to its hydroxide form while the sample anions are eluted. The released sample anions and excess hydroxide ions generated at the upstream located cathode are routed to the downstream end of the column 36 and combine with the hydronium ions generated at the downstream located anode to form the highly conductive acid of the sample anions and relatively non-conductive water, respectively. The effluent from column 36 (e.g., the column effluent), which contains the sample anions in their highly conductive acid form and the relatively non-conductive water, is then routed downstream to a detector 42 in which the sample anions are detected. The detector is preferably a conductivity detector, such as the ALLTECH Model 350 Conductivity Detector. The sample ions detected at the detector may also be quantified by a data system (not shown). The data system is preferably a computer based integrator, such as the HEWLETT-PACKARD General Purpose Chemstation.

Preferably, the effluent from the detector (e.g., detector effluent) is then routed from the detector 42 through a backpressure regulator 44. The backpressure regulator 44 keeps the gaseous $H_2$ and $O_2$ bubbles formed at the cathode and anode, respectively, small enough so that they do not interfere with the detector 42. The backpressure regulator is preferably a spring-energized diaphragm system that maintains constant backpressure on the system regardless of flow rate, such as the ALLTECH backpressure regulator. The detector effluent can then be routed from the backpressure regulator 44 to waste 46. Alternatively, before being routed to the detector 42, the column effluent may be routed through a gas-permeable membrane tube (not shown) positioned between the analytical column 36 and the detector 42.

In that way, the gas bubbles generated by the electrolysis of water may be released through the gas permeable membrane to the atmosphere.

In a preferred embodiment, the detector effluent is routed from the back-pressure regulator to an ion exchange bed 45. In anion analysis, the ion exchange bed may be packed with anion exchange packing material (not shown). The anion exchange packing material preferably comprises exchangeable hydroxide ions, and is selected as previously described with respect to column 36. The sample anions replace the exchangeable hydroxide ions on the anion exchange packing material in the ion exchange bed, and the released hydroxide ions combine with the hydronium counterions of the sample anions to form water. The water may then be routed from the ion exchange bed 45 to the water-containing eluant source 30. In this manner, a self-sustaining eluant source is established. Of course, the anion exchange resin in the ion exchange bed 45 will eventually become exhausted, and thus it will need to be periodically replaced or, in the alternative, regenerated according to the methods described herein.

A variety of anions can be separated, detected, and analyzed according to the foregoing method. Examples include chloride ions, nitrate ions, bromide ions, nitrite ions, phosphate ions, sulfate ions, as well as other organic and inorganic anions. FIGS. 5A and 5B are schematic views of column 36 when used in the foregoing method of anion analysis by electroelution (chromatography. In FIG. 5A, the sample anions ($X^-$) are retained on the anion exchange packing material 46 that is packed in column 36. Turning to FIG. 5B, when the power source (not shown) is turned on, hydroxide ions generated at the upstream located cathode of the column 36 are routed through the anion exchange packing material and displace the retained sample anions $X^-$. The released sample anions ($X^-$) combine with the hydronium ions generated at the downstream located anode of column 36 to form the highly conductive acid of the sample anions (HX). Additionally, the excess hydroxide ions generated at the upstream located cathode combine with the hydronium ions generated at the downstream located anode to form the relatively low conductive water. Thereafter, the sample anions in their acid form are routed with water from the column 36 to the detector (not shown) where the sample anions are detected.

Based on the foregoing discussion, those skilled in the art will appreciate that the electrodes can be located either outside of or inside the column 36. The only necessary condition with respect to the placement of the electrodes is that at least a portion of the chromatography packing material (anion exchange packing material in the foregoing embodiment) is disposed between the two electrodes, and that fluid flow through the column is from one of the electrodes to the other. Thus, when it is said that the electrode is positioned at an upstream end of the column, it does not necessarily mean that the electrode is actually located in the column. To the contrary, it is simply meant that the electrode is located between the fluid source and the other electrode. Similarly, by the term "downstream end" of the column, it is meant that the electrode is located on the side opposite the fluid source relative to the other electrode. Again, the electrode is not necessarily positioned in the column itself. Thus, fluid flow is always from the "upstream" located electrode to the "downstream" located electrode.

Without being restricted to theory, it is presently believed that the electrical current in column 36 is generated between the two electrodes via ion transport along the chromatography packing material (not shown) in the column 36. However, where the packing material is not capable of ion transport, it is presently believed that ion transport takes place via the mobile phase. This electric current via ion transport surprisingly occurs even when the chromatography packing material and the eluant may not inherently be electrically conductive. Because the electric current is generated by ion transport along the chromatography packing material in the effluent flow channel (not shown) of column 36, the electric current through column 36 is in the same direction as fluid flow through the column 36.

As those skilled in the art will understand, the electrical voltage generated in column 36 must be of sufficient strength for the electrolysis of water to occur. The strength of the current generated in column 36 is directly proportional to the voltage applied at the electrodes, the cross-section area of the electrodes, and the capacity of the packing material in column 36 (e.g. the higher the capacity of the packing material, the lower the resistance is in the column 36). The strength of the current in column 36 is inversely related to the distance between the two electrodes.

The above method and apparatus can also be adapted for the separation, detection, and analysis of sample cations as well. For cation analysis, the column 36 is packed with cation exchange packing material. The cation exchange packing material preferably comprises exchangeable hydronium ions. Preferred cation exchange packing materials include acid functionalized organic and inorganic particles, such as phosphoric acid functionalized organic or inorganic particles, carboxylic acid functionalized organic or inorganic particles, sulfonic acid functionalized organic or inorganic particles, and phenolic acid functionalized organic or inorganic particles. The cation exchange particles may be packed into the column in either resin form or impregnated into a membrane. The most preferred cation exchange packing materials are sulfonic acid functionalized particles. Most preferably, the cation exchange packing material is packed in the column in resin form.

In cation analysis, the apparatus of FIG. 4 is further reconfigured so that the anode (not shown) is positioned at the upstream end of the column 36 and the cathode (not shown) is positioned at the downstream end of the column 36. Thus, when an electric current of sufficient strength is applied, hydronium ions are generated at the upstream located anode 36. The hydronium ions are then routed across the cation exchange packing material and displace the previously retained sample cations in the column 36. The released sample cations and excess hydronium ions generated at the upstream located anode combine with the hydroxide ions generated at the downstream located cathode to form the highly conductive bases of the sample cations and water, respectively. The sample cations, in their basic form, and relatively non-conductive water are then routed to detector 42 where the sample cations are detected. Finally, the detector effluent is preferably routed through ion exchange bed 45, which comprises cation exchange packing material (not shown). The cation exchange packing material preferably comprises exchangeable hydronium ions, and is selected as described above. The sample cations displace the hydronium ions and are retained in the ion exchange bed 45, and the released hydronium ions combine with the hydroxide counterions of the sample cations to form water. The ion exchange bed effluent (which comprises water), is then routed to the water containing eluant source.

With reference back to FIG. 4, in an especially preferred embodiment of the present invention both cation exchange packing material (not shown) and anion exchange packing material (not shown) is packed in column 36. Similarly, ion exchange bed 45 is packed with both cation exchange packing material (not shown) and anion exchange packing material (not shown). Preferably, the cation and anion exchange packing material comprise exchangeable hydronium and hydroxide ions, respectively, arid are selected as previously described. In this embodiment, both cations and anions in the same test sample may be analyzed according to the foregoing method of electroelution chromatography. However, this configuration is also preferred even when only cations or only anions being detected as well.

However, when it is desired to separate both anions and cations in the same sample, a sample comprising anions and cations to be separated is routed through column 36. The sample cations are retained in column 36 on the cation exchange resin and the sample anions are retained in column 36 on the anion exchange resin. The polarity of column 36 is arranged depending on whether cations or anions are to be eluted first. Where it is desired to elute the cations first, the anode (not shown) is located at an upstream end of column 36 and the cathode (not shown) is located at a downstream end of the column 36. The power source 38 is turned on to generate an electric current across the anion exchange resin and cation exchange resin in column 36. Hydronium ions are generated at the upstream located anode by the electrolysis of the water-containing eluant as previously described. Similarly, hydroxide ions are generated at the downstream located cathode as previously described. The hydronium ions are routed through column 36, displacing the retained sample cations and simultaneously regenerating the cation exchange packing material back to its hydronium form. The released sample cations and the excess hydronium ions generated at the upstream located anode combine with hydroxide ions generated at the downstream located cathode to form the highly conductive bases of the sample cations and the relatively non-conductive water, respectively.

The sample cations (in their base form) and water are then routed to detector 42 where the sample cations are detected. The detector effluent may then be routed to the ion exchange bed 45 where the sample cations are retained by displacing the hydronium ions on the cation exchange packing material in the ion exchange bed 45. The hydronium ions displaced from the cation exchange packing material combine with the hydroxide counterions of the sample cations to form water, which may then be routed to the water-containing eluant source 30.

After the sample cations have been detected, the polarity of column 36 is reversed, so that the cathode (not shown) is located at an upstream end of column 36 and the anode (not shown) is located at a downstream end of the column 36. Hydroxide ions are generated at the upstream located cathode and hydronium ions are generated at the downstream located anode by electrolysis of the water-containing eluant as previously described. The hydroxide ions are routed through column 36, displacing the retained sample anions and simultaneously regenerating the anion exchange packing material back to its hydroxide form. The released sample anions and the excess hydroxide ions generated at the upstream located cathode combine with the hydronium ions generated at the downstream located anode to form the highly conductive acids of the sample anions and the relatively non-conductive water, respectively.

The sample anions (in their acid form) and water are routed to the detector 42 where the sample anions are detected. The detector effluent may then be routed to the ion exchange bed 45 where the sample anions are retained by displacing the hydroxide ions on the anion exchange packing material in the ion exchange bed 45. The displaced hydroxide ions then combine with the hydronium counterions of the sample anion to form water, which may then be routed to the water-containing eluant source 30.

In another embodiment of the present invention, two columns as illustrated in FIG. 1 can be arranged in series for use in methods of detecting cations and anions in the same test sample. With reference to FIG. 6, a water-containing eluant source 30 (again, preferably deionized water) is introduced through a high pressure liquid chromatography (HPLC) pump 32. A test sample containing both anions and cations to be detected is injected through an injector 34, and is carried by the eluant to a first column 36 of the present invention, which is packed with anion exchange packing material (not shown). The anion exchange packing material preferably comprises exchangeable hydroxide ions, and is selected as previously described.

The sample anions displace the hydroxide ions on the anion exchange resin and are retained in the first column 36. The first column effluent, which contains the sample cations and displaced hydroxide ions, is routed to a second column 136. Column 136 is packed with cation exchange packing material preferably comprising exchangeable hydronium ions, and is selected as previously described. The sample cations displace the hydronium ions on the cation exchange packing material and are retained in the column 136. The released hydronium ions neutralize the hydroxide ions in the first column effluent to form water. The water is then preferably routed through the detector 42 (giving no signal), through an ion exchange bed 46, through valve 48 and back to the eluant source 30.

An electric current sufficient to electrolyze water is then generated in column 36 across the anion exchange packing material by turning on electric power supply 38. The cathode (not shown) of the column 36 is located at an upstream end and the anode (not shown) is located at a downstream end of the column 36. The water-containing eluant undergoes electrolysis at the upstream located cathode thereby generating hydroxide ions and hydrogen gas as previously described. The hydroxide ions generated at the upstream located cathode are routed through the column 36 and displace the retained sample anions on the anion exchange packing material thereby eluting the sample anions from column 36.

At the downstream located anode of the column 36, hydronium ions and oxygen gas are generated as previously described by the electrolysis of the water-containing eluant. The released sample anions from column 36 and the excess hydroxide ions generated at the upstream located anode of the column 36 combine with the hydronium ions generated at the downstream located cathode of the column 36, to form the highly conductive acids of the sample anions and relatively non-conductive water, respectively.

The acids of the sample anions and water from column 36 are routed through column 136 unretained to detector 42, in which the sample anions are detected and quantified by a data system 43. The bubbles formed by the hydrogen gas and oxygen gas generated at the cathode and anode, respectively, of the column 36 are kept small enough by back pressure regulator 44 so that they do not interfere with the detector 42.

The detector effluent is then preferably routed from the detector 42 through back pressure regulator 44 to an ion exchange bed 46 comprising ion exchange packing material having exchangeable hydronium and exchangeable hydroxide ions. The ion exchange bed is preferably of high-purity such as those used to produce deionized water. The sample anions displace the hydroxide ions and are retained in the ion exchange bed 46. The displaced hydroxide ions neutralize the resulting hydronium counterions of the sample anions to form water, which is preferably routed through valve 48 back to the eluent source 30.

Once the sample anions have been detected, an electric current sufficient to electrolyze water is then generated in column 136 across the cation exchange packing material by turning on electric power source 138. The anode (not shown) is positioned at an upstream end of the column 136 and the cathode (not shown) is located at a downstream end of the column 136. The water containing eluant undergoes electrolysis at the upstream located anode of the column 136 thereby generating hydronium ions. The hydronium ion; are then routed through the column 136 and displace the previously retained sample cations on the cation exchange resin thereby eluting the sample cations from column 136.

At the downstream located cathode (not shown) of column 136, hydroxide ions and hydrogen gas are generated as previously described by the electrolysis of the water-containing eluant. The released sample cations and the excess hydronium ions generated at the upstream located cathode of the column 136 combine with the hydroxide ions generated at the downstream located anode of the column 136, to form the highly conductive bases of the sample cations and relatively non-conductive water, respectively.

The sample cations (in their base form) and water are then routed from column 136 to detector 42, in which the sample cations are detected and quantified by data system 43. Again, the bubbles formed by the hydrogen gas and oxygen gas generated at the cathode and anode, respectively, of the column 136 are kept small enough by the backpressure regulator 44 so that they do not interfere with the detector 42.

The detector effluent is then preferably routed from the detector 42 through backpressure regulator 44 to the ion exchange bed 46. The sample cations displace the exchangeable hydronium ions in the ion exchange bed 46 and are retained therein. The displaced hydronium ions neutralize the hydroxide counterions of the sample cations to form water, which is preferably routed through valve 48 back to eluant source 30.

FIG. 7 is a chromatogram of a test sample containing both anions and cations separated pursuant to the foregoing method and apparatus of the present invention. The first series of peaks represent the sample anions that are eluted when power is applied and an electric current is generated across the anion exchange packing material in column 36. The second series of peaks represent the sample cations that are eluted and detected when power is applied and an electric current is generated across the cation exchange packing material in column 136.

As those skilled in the art will recognize, the foregoing apparatus and method can be easily reconfigured so that the column 36 is packed with cation exchange packing material and the anode is located at an upstream end and the cathode is located at a downstream end of the column 36, and column 136 is packed with anion exchange packing material and the cathode is located at a upstream end and the anode is located at a downstream end of the column 136.

The foregoing methods and apparatuses provide many advantages. For example, the strength of the current applied in the columns 36 and 136 will determine the concentration of hydroxide and hydronium ions generated in these columns. The higher the current, the greater the concentration of hydroxide or hydronium ions and the easier and quicker the sample anions and cations will be eluted. Thus, gradients are therefore possible through time-based current programming in the anion and cation columns. Moreover, the foregoing method can be configured as a closed loop system. Additionally, simultaneous cation and anion analysis is possible with high sensitivity and low background noise. Moreover, water dips, and unretained counter-cation peaks, and unretained counter-anion peaks often pre sent in traditional ion chromatography methods may be reduced and even eliminated.

The methods and apparatuses previously described can also be used in methods and apparatuses for the electroelution of proteins, as well as any other test sample whose affinity for chromatographic packing material is affected by pH changes and/or ionic strength changes. Proteins and many other test samples retain on affinity stationary phases by biological recognition, on reversed phases by hydrophobic interactions, on ion-exchange or chelation packing materials by charge interactions, by size on size exclusion packing materials, by hydrophobic interactions on hydrophobic packing materials, and by normal phase interactions on normal phase packing materials. All of these retention mechanisms may be mediated by ionic strength and/or pH. By using the electrolysis of water as discussed in the foregoing embodiment, the hydrogen and hydroxide ion concentration in the column illustrated in FIG. 1 can be controlled, thereby permitting the control of the pH and ionic strength inside the column. Thus, by packing the chromatography column of the present invention with an ion-exchange, affinity stationary phase, reversed phase, size exclusion, chelating, hydrophobic, or normal phase chromatography packing material, proteins or other samples can be retained when no power is applied to the column. However, when power is applied to generate hydronium ions (decrease pH) or hydroxide ions (increase pH) within the column, the resulting ionic strength and pH change may be used to elute the retained protein (or other samples) from the column. Thus, the column of the present invention can be used to separate and purify a wide range of compounds on both an analytical and preparative scale.

Suitable packing materials for use in the foregoing embodiment include Protein A affinity packing material as the affinity phase packing material; C-18 reversed phase packing material as the reversed phase packing material; Chelex-100 from Bio-Rad in the chelating packing material; ALLTECH Macrosphere GPC as the size exclusion packing material; SYNCHROM SynChropak HIC as the hydrophobic packing material; and ALLTECH Alltima Silica as the normal phase packing material.

Additionally, as discussed below, the column of the present invention can also be used as a self-regenerating solid phase chemical suppressor in various apparatuses and chromatography methods.

B. Electrochemically Regenerated Solid Phase Chemical Suppressor

1. System Configurations for Anion Analysis

FIGS. 5A–5D are schematic views of various preferred apparatus configurations for a preferred method of ion analysis using the column illustrated in FIG. 1 as a self-regenerating solid phase chemical suppressor. With reference to FIG. 8A, an eluant source 202 is in fluid connection with a pump 204. Downstream from the pump 204 is an injector 206 where a test sample can be added to the system. Located downstream from the injector 206 is an analytical (or chromatography) column 208 where separation of the ions in the test sample occurs. In anion analysis, a low-capacity anion exchange column is preferably used. For cation analysis, a low-capacity cation exchange column is preferably used.

Located downstream from, and in fluid connection with, the analytical column 208, is a 10-port switching valve 210. The switching valve is preferably of the metal-free rotary type. In connection with the 10-port switching valve 210 are two columns, 212 and 214, respectively, as illustrated in FIG. 1. Connected to columns 212 and 214 are electrical power sources 216a and 216b, respectively. One power source connected to both columns 212 and 214 may be used as well. This embodiment generally requires lower voltage than the foregoing methods of electroelution chromatography because the capacity of the chromatography packing materials in this embodiment is greater (e.g. lower resistance), and thus lower voltages are capable of generating a current sufficient for the electrolysis of water. A preferred power source is the KENWOOD PR 36-1.2 power supply. When the column illustrated in FIG. 1 is used as a suppressor, the power source should be capable of delivering about 1–100 volts to the electrodes, more preferably about 10–90 volts, and most preferably about 3–15 volts. Finally, a conductivity detector 218 is connected with 10-port switching valve 210. As described in more detail below, the column illustrated in FIG. 1 is adapted for use as a self-regenerating solid phase chemical suppressor in the foregoing configuration.

Still with reference to FIG. 8A, an aqueous eluant source 202 introduces eluant through a HPLC pump 204. A test sample containing anions to be detected is injected through injector 206, and is routed by the eluant to analytical (or chromatography) column 208. In the present embodiment (e.g., anion analysis) the eluant may comprise solutions of sodium carbonate, sodium bicarbonate, sodium hydroxide or some other base that is converted to a weak acid by counterion exchange with hydronium ions. The most preferred eluant for anion analysis are solutions of sodium hydroxide.

The analytical column 208 is preferably packed with anion exchange packing material (not shown). Suitable anion exchange packing materials comprise particles of primary, secondary, tertiary, or quaternary amino functionalities, either organic or inorganic. The preferred anion exchange packing materials comprise quaternary amino functionality organic or inorganic particles. These anion exchange particles may either be packed into the column in resin form or impregnated into a membrane. Preferably, the packing material is in resin form.

Different anions in the test sample have differing affinities for the anion exchange packing material in the analytical column 208. The stronger the affinity of a particular type of anion for the packing material in the analytical column 208, the longer that type of anion will be retained in the column 208. Conversely, the weaker the affinity of a particular type of anion for the, packing material in the analytical column 208, the shorter that particular type of anion will be retained in the column 208. Thus, because different anions have different affinities for the packing material in column 208, the sample anions are eluted at different speeds from the column 208 and are therefore separated or resolved.

The effluent from analytical column 208 (hereinafter referred to as "chromatography effluent") is routed from the column 208 through 10-port switching valve 210 to column 212. In this embodiment, the column 212 is adapted for use as a suppressor in a method of anion analysis. The column 212 is packed with cation exchange packing material (not shown). Preferred cation exchange packing materials include acid functionalized organic or inorganic particles, such as phosphoric acid functionalized organic or inorganic particles, carboxylic acid functionalized organic or inorganic particles, phenolic acid functionalized organic or inorganic particles, and sulfonic acid functionalized inorganic or organic particles. The cation exchange particles may either be packed into the column in resin form or impregnated into a membrane. The most preferred cation exchange packing materials are sulfonic acid functionalized inorganic or organic particles in resin form.

Two ion-exchange reactions take place in the suppressor 212:

1. Eluant:

(where the eluant is sodium hydroxide and the cation exchange packing material comprises sulfonic acid functionalized particles):

$$NaOH + Resin\text{-}SO_3^-H^+ \rightarrow Resin\text{-}SO_3^-Na^+ + H_2O$$

2. Analyte:

$$NaX + Resin\text{-}SO_3^-H^+ \rightarrow Resin\text{-}SO_3^-Na^+ + HX$$

(where X=anions such as Cl, $NO_2$, Br etc.)

The sodium ions in the high conductivity eluant are removed by ion exchange with the hydronium ions present on the cation exchange packing material in the column 212. The high conductivity sodium hydroxide eluant is thus converted to the relatively non-conductive water (the sample counterions are also suppressed by ion-exchange with hydronium ions on the cation exchange packing material). This, of course, reduces the background noise from the eluant (and sample counterions) when the sample anions are ultimately detected in the detector 218. The sample anions are converted into their highly conductive acid form by exchanging their counterions with hydronium ions on the cation exchange packing material in the column 212. As can be ascertained from the above reactions, the eluant in anion analysis can be any salt solution that forms a weakly conductive acid in the suppressor 212. Examples of suitable eluants include aqueous solutions of sodium hydroxide, sodium carbonate/bicarbonate, and sodium tetraborate. The eluant must further comprise water, however, to feed the electrolysis in the methods of the invention.

After the eluant has been converted to its weak acid and the sample anions to their highly conductive acids in the column 212, the suppressor effluent is routed through the 10-port switching valve 210 to detector 218 where the sample anions are detected. Data from the detection of the sample anions is preferably recorded on a chart, graph, an integrator, a computer, or other recording means (not shown). The effluent from the detector 218 (hereinafter referred to as "detector effluent") is then routed through 10-port switching valve 210, and column 214 to waste.

When the cation exchange packing material in suppressor 212 is exhausted (e.g., completely converted from the hydrogen to sodium form), a sharp increase in the conductance of the suppressor effluent is observed. Before this happens, the 10-port switching valve 210 is switched to the configuration depicted in FIG. 8B. While using the column 214 to suppress the chromatography effluent in the same manner as previously described with respect to column 212, the detector effluent is recycled back through 10-port switching valve 210 to the exhausted suppressor 212 to regenerate it as follows.

A power source 216a is turned on thereby generating an electric current sufficient for the electrolysis of water across the exhausted cation exchange packing material in suppressor 212. Suppressor 212 is configured so that the anode (not shown) is positioned at the upstream end and the cathode (not shown) is positioned at the downstream end of the suppressor 212. The detector effluent (which contains water) undergoes electrolysis at the upstream located anode of suppressor 212 as previously described:

$$2H_2O \rightarrow 4H^+ + O_2 + 4e^+$$

Hydronium ions and oxygen gas are thus generated at the upstream anode of suppressor 212. Since the detector effluent is flowing from the anode side to the cathode side of the suppressor 212, the hydronium ions are routed across the exhausted cation exchange packing material in suppressor 212 converting it back to the hydrogen form according to the following reaction:

$$Resin\text{-}SO_3^-Na^+ + H^+ \rightarrow Resin\text{-}SO_3^-H^+ + Na^+$$

The oxygen gas and displaced sodium ions (and sample counterions) from suppressor 212 are then routed through 10-port switching valve 210 to waste.

At the downstream located cathode of suppressor 212, water undergoes electrolysis as previously described:

$$2H_2O + 2e^- \rightarrow H_2 + 2OH^-$$

Hydroxide ions and hydrogen gas are thus generated at the downstream end of suppressor 212. The hydroxide ions and hydrogen gas generated in suppressor 212 are routed through 10-port switching valve 10 to waste.

Alternately, the systems waste products may be recycled. As can be appreciated from the above chemical reactions, the regeneration process liberates exactly the same mass of eluant ions consumed during the suppression process. Because the process is quantitative, routing the waste products from switching valve 10 back to eluant source 2 on a continuous basis will result in continuous reconstitution of the original eluant (in this embodiment sodium hydroxide), eliminating chemical waste.

Power source 216a is left on long enough to regenerate the cation exchange packing material in suppressor 212. Once the suppressor 212 is regenerated, the power source is turned off. The detector effluent is still preferably routed through the suppressor 212, however, for a time sufficient to purge any remaining gas bubbles and electrolysis products in suppressor 212, and to equilibrate the column. Once the suppressor 212 is regenerated and equilibrated, it is ready for use as the "active" suppressor when suppressor 214 becomes exhausted. Once suppressor 212 is ready to go back on line, the analytical column effluent is re-routed to suppressor 212 and suppressor 214 is regenerated in the same manner as previously described with respect to suppressor 212.

The foregoing arrangement allows endless cycling between the two suppressors 212 and 214 for continuous instrument operation without interruption or suppressor replacement. The system is easily automated using automatic valves and power supplies to provide unattended operation for extended periods. No regenerant reagents or pumps are required and no chemical waste (other than the detector effluent generated on any IC system) is created. The system can be used without fragile membranes and will tolerate high backpressures for greater reliability than membrane-based devices. The system is furthermore compatible with electroactive eluants and organic solvents and operates equally well with all common SIC eluants overcoming the drawbacks associated with prior self-regenerating suppressors.

Figure 8C:
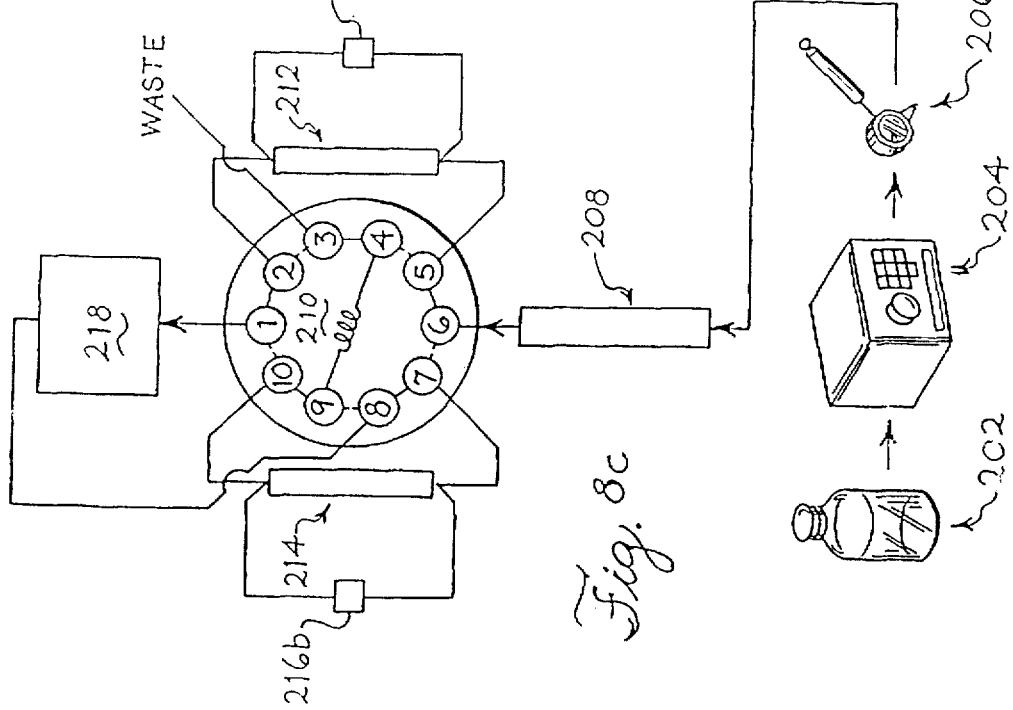

With reference to FIGS. 8C and 8D, an alternative 10-port switching valve scheme is depicted. In FIG. 8C, suppressor 212 is the active suppressor as described previously. Before suppressor 212 is exhausted, the analytical column effluent is re-routed as depicted in FIG. 8D. In FIG. 8D, the suppressor 214 is the active suppressor and the detector effluent is routed from the detector 218 through the 10-port switching valve 210 to suppressor 212 to regenerate the suppressor 212 by electrolysis of the detector effluent as previously described. As those skilled in the art will appreciate, to regenerate the cation exchange resin in either suppressors 212 or 214, it is critical that the anode is located at an inlet (upstream) side of the suppressor.

2. Alternate Valve Schemes

Figure 9A:
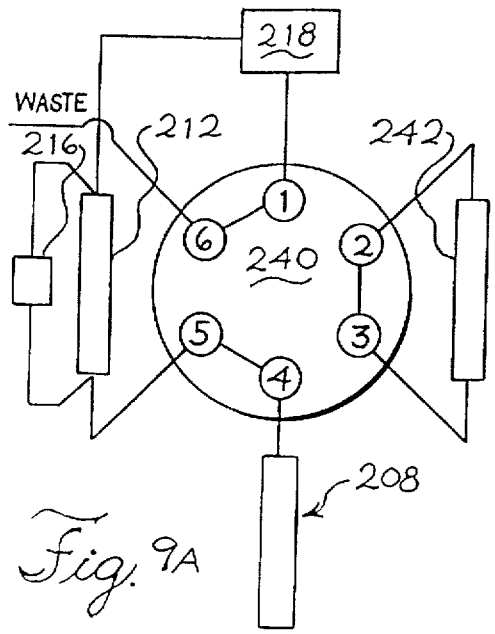
FIGS. 9A and 9B are schematic views of a chromatography apparatus where the column of FIG. 1 is used as a solid phase chemical suppressor.
Figure 9B:
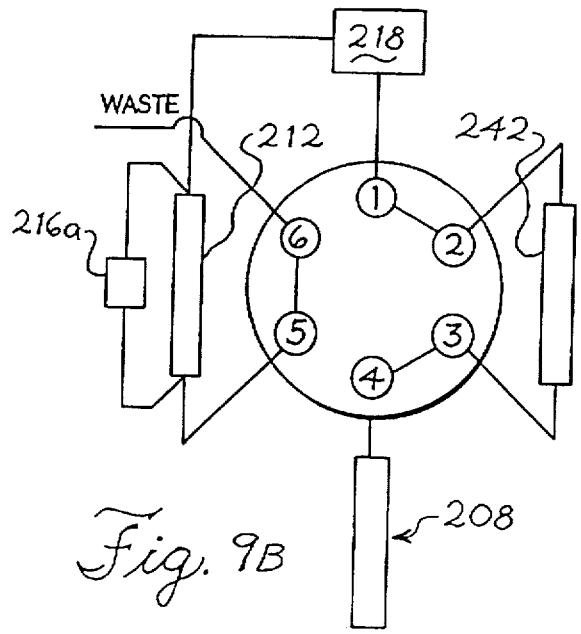

Valve schemes other than the 10-port switching valve described above may also be used in the present invention. With reference to FIGS. 9A and 9B, a 6-port valve 240 may be used. In FIG. 9A, the chromatography effluent is routed from analytical column 208 through 6-port switching valve 240 to suppressor column 212 and to the detector 218 where the sample ions are detected. With reference to FIG. 9B, when the column 212 is exhausted and needs to be regenerated, the 6-port switching valve 240 is switched so the column effluent is routed from analytical column 208 to a packed bed suppressor 242 with strong cation exchange resin in the hydrogen form (i.e., during anion analysis). The cation exchange resin may be as previously described. In the packed bed suppressor 242 the analytical column effluent (aqueous sodium hydroxide or aqueous sodium carbonate/ bicarbonate) is converted to water or carbonic acid. The packed bed suppressor effluent is then routed through the detector 218 to the exhausted column 212, where the water in the packed bed suppressor effluent feeds the electrolysis at column 212 to regenerate the suppressor column 212.

In this scheme, only one suppressor column 212 is used for the analysis. The electrochemical regeneration of the suppressor column 212 can be done between injections, after each injection before the sample anions elute from the analytical column 208, or whenever necessary. The packing material in the packed bed suppressor 242 may be coated with dye to provide color indication of its condition. The packed bed suppressor 242 may need to be replaced only once a month or less depending on its total capacity. Since the packed bed suppressor 242 is not used during the chromatographic analysis, its size is not limited.

Figure 10A:
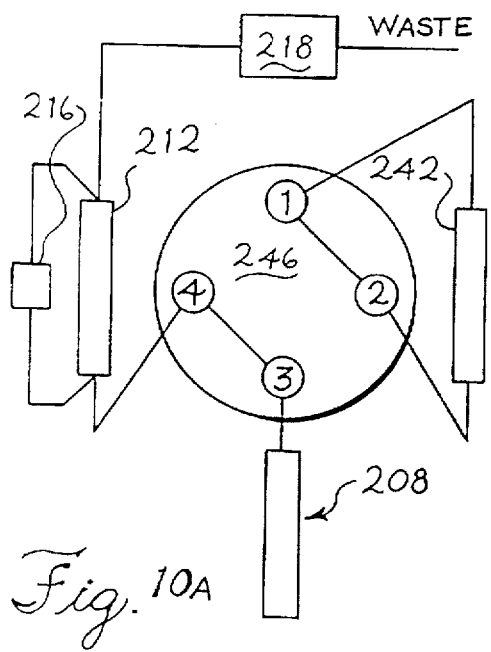
FIGS. 10A and 10B are schematic views of the chromatography apparatus illustrated in FIGS. 9A and 9B, except that a different valve scheme is shown.
Figure 10B:
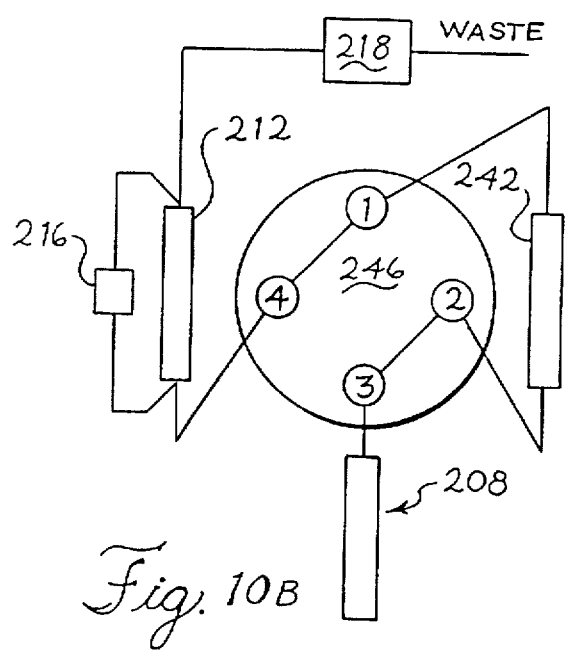

In another aspect of this invention and as depicted in FIGS. 10A and 10B, the system may use a 4-port switching valve 246. In FIG. 10A, the analytical column effluent is routed from the analytical column 820 through 4-port switching valve 246 to suppressor column 212. The suppressor effluent is then routed to the detector 218 (where the sample anions are detected) and then to waste. When the suppressor column 212 is exhausted and needs to be regenerated, the 4-port switching valve 246 is switched so that the analytical column effluent is routed through packed bed suppressor 242 with strong cation exchange resin in the hydrogen form. The analytical column effluent is converted to water or carbonic acid in the suppressor 242. The packed bed suppressor effluent is then routed through 4-port switching valve 246 to column 212 (see FIG. 10B). The water in the packed bed suppressor effluent feeds the electrolysis in column 212 to regenerate the column 212 as previously described. A disadvantage of this design compared to the 6-port switching valve 240 or the 10-port switching valve 210 configurations is that the gases generated during electrolysis will pass through the detector 218 before going to waste. Gas bubbles may thus become trapped inside the detector 218, creating extreme baseline noise.

3. Suppressor for Cation Analysis

As those skilled in the art will appreciate, if the polarity of the previously described suppressor columns are reversed and the chromatography packing materials are changed from cation exchange packing material to anion exchange packing material, the same system configurations as previously described may be used as cation suppressors.

In cation analysis, the eluant is usually a solution of an acid such as hydrochloric acid, nitric acid, diaminopropionic acid hydrochloride, or methanesulfonic acid. The anion exchange packing material may be either anion exchange resins or membranes impregnated with anion exchange particles. Preferred anion exchange packing materials include primary, secondary, tertiary, or quaternary amine functionalized inorganic or organic particles. The most preferred anion exchange packing materials comprise quaternary amine functionalized inorganic or organic particles.

In cation analysis, the following reactions take place in the suppressor column (where hydrochloric acid is the eluant and the anion exchange material comprises a quaternary amine functionalized particle):

1) Eluant:

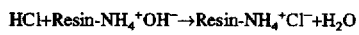

2) Analyte:

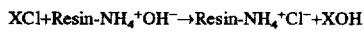

where X=cations (Na, K, Li, Mg, Ca, etc.)

To regenerate the suppressor column in cation analysis, the position of the anode and cathode is opposite of that for anion analysis (i.e., the cathode is placed on the side of the suppressor where the detector effluent enters the suppressor column). During electrolysis, the following reaction takes place at the cathode:

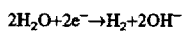

The released hydroxide ions are routed through the column to convert the chloride form resin (exhausted anion exchange material) back to the hydroxide form according to the following reaction:

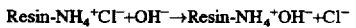

The various valve schemes previously described can also be used for cation analysis.

4. High Purity Eluant Chromatography

The column illustrated in FIG. 1 can also be advantageously employed in a method and apparatus for generating a high purity eluant. With reference to FIG. 11A, a deionized water source 100 is provided. A pump 102 as previously described is connected to water source 100. Downstream from pump 102 is a sample injector 104. Downstream from the sample injector 104 are three columns 112, 120 and 122, which are arranged in series. Column 112 is preferably constructed as illustrated in FIG. 1. An electrical power source 116 is connected to column 112. Column 120 is an analytical (e.g. chromatography) column packed with chromatography packing material (not shown). Column 122 is also preferably constructed as illustrated in FIG. 1, and is adapted for use as a solid-phase chemical suppressor in this embodiment. Located downstream from columns 112, 120 and 122 is a conductivity detector 118, which is as previously described. Finally, downstream from detector 118, is a backpressure valve 144 and an ion exchange bed 146, which are also as previously described.

For anion analysis, column 112 is adapted for use as an eluant generating source and is packed with cation exchange packing material (not shown). The packing material preferably comprises exchangeable sodium ions. Column 120 is packed with anion exchange packing material (not shown) which is selected as previously described. Finally, column 122 is packed with cation exchange packing material (not shown) comprising exchangeable hydronium ions, and is selected as previously described. The electric power source 116 is connected to an anode (not shown) which is positioned at the upstream end of column 112, and a cathode (not shown) which is positioned at the downstream end of the column 112. A high purity eluant for anion analysis is generated as follows.

The water-containing eluant is routed through eluant generating column 112. Power source 116 is turned on thereby generating an electric current sufficient to electrolyze water across the sodium form cation exchange packing material (not shown) in column 112. At the anode (not shown), which is located at the upstream end of column 112, the water-containing eluant undergoes electrolysis thereby generating hydronium ions as previously described. At the cathode (not shown), which is located at the downstream end of column 112, the electrolysis of the water-containing eluant generates hydroxide ions as previously described. The hydronium ions generated at the upstream end of the column 112 flow across the sodium form cation exchange packing material and displace the sodium ions. The released sodium ions combine with the hydroxide ions generated at the downstream end of the column 112 to form a high purity sodium hydroxide eluant.

The sample anions (which may be injected either before or after eluant generating column 112), and the high purity sodium hydroxide eluant are then routed through analytical column 120, where the sample anions are then separated. The analytical column effluent is then routed from column 120 to solid phase chemical suppressor 122. The sample anions are converted to their highly conductive acids by exchanging their counterions for the hydronium ions on the hydronium form cation exchange packing material in suppressor 122. Similarly, the sodium hydroxide eluant is converted to relatively non-conductive water by exchanging its sodium ions for the hydronium ions on the hydronium-form cation exchange material in suppressor 122. The suppressor effluent is then routed from suppressor 122 to detector 118 where the sample anions are detected. The detector effluent is then routed through back-pressure regulator 144 to ion exchange bed 146. For anion analysis, ion exchange bed 146 comprises anion exchange packing material comprising exchangeable hydroxide ions, and is selected as previously described. The sample anions displace the hydroxide ions in the ion exchange bed 146. The released hydroxide ions combine with the hydronium counterions of the sample anions to form water. The water may then be routed back to water source 100.

As those skilled in the art will appreciate, in addition to generating a high purity eluant, the foregoing method can suitably be used in a method of gradient elution chromatography by controlling the amount of sodium hydroxide eluant generated in column 112. The higher the current in column 112, the greater the concentration of sodium hydroxide that will be generated in column 112.

When columns 112 and 122 are exhausted, i.e. the ion exchange packing maternal is converted to the hydronium form and sodium form, respectively, they may be regenerated, either on-line or off-line. On-line regeneration may be accomplished according to the following steps. With reference to FIG. 11B, the water-containing eluant is rerouted and routed to column 122. An electrical power source 123 is provided. The power-source 123 is connected to an anode (not shown), which is positioned at the upstream end of column 122, and a cathode (not shown) which is positioned at the downstream end of column 122. The water-containing eluant enters column 122 at the anode (not shown) end of column 122. Power source 123 is turned on thereby generating an electric current sufficient to electrolyze water across the cation exchange packing material (now in the sodium form) in column 122. Hydronium ions are generated at the anode end of column 122 by the electrolysis of the water-containing eluant as previously described. Also, hydroxide ions are generated at the cathode end of the column 122 by the electrolysis of water as previously described. The hydronium ions are routed across the sodium form cation exchange material in column 122 and displace the sodium ions thereby converting the cation exchange resin back to the hydronium form. The released sodium ions and the excess hydronium ions generated at the anode end of column 122 combine with the hydroxide ions generated at the cathode end of column 122 to form a high purity sodium hydroxide and water eluant.

The high purity sodium hydroxide eluant (as well as any sample anions to be detected) is routed through analytical column 120, where any sample anions are separated as previously discussed, and then to column 112. The exhausted cation exchange packing material in column 112 is in hydronium form. The hydronium ions on the exhausted cation exchange material in column 112 are displaced by sodium ions in the sodium hydroxide eluant thereby regenerating the cation exchange packing material back to its sodium form. The released hydronium ions combine with the hydroxide ions in the eluant to form relatively low conductivity water. The water (and sample anions) may then be routed to a detector (not shown) where the sample anions are detected. The detector effluent may then be routed through an ion exchange bed (not shown) where the sample anions are retained and hydroxide ions are released and combine with the hydronium counterions of the sample anions to form water as previously described. The water may then be routed to the water source 100.

The foregoing method and apparatus can also be used for generating a high purity eluant for cation analysis. In this embodiment, the column 112 is packed with anion exchange packing material, preferably comprising exchangeable chloride ions. Column 120 is packed with cation exchange packing material preferably comprising exchangeable hydronium ions, and suppressor column 122 is packed with anion exchange packing material comprising exchangeable hydroxide ions.

FIG. 11C is a schematic of an alternative method and apparatus for generating a high purity eluant and capable of a gradient. In this embodiment, the eluant generating column 113 may comprise a disposable cartridge packed with either anion or cation exchange packing material as previously described with respect to eluant generating column 112 (see FIG. 11a and accompanying text in specification). Also, the sample is injected downstream from the eluant generating column 115.

5. Combination with Hydrophobic Packing Material (Hydrophobic suppressor)

The column illustrated in FIG. 1 can also be used with a hydrophobic suppressor column, which is particularly useful in methods of inorganic anion analysis using an organic anion as the eluant. With reference to FIG. 12A, the sample anions and the eluant (which comprises an organic anion) are routed through analytical column 8. The analytical column 8 is packed with anion exchange packing material (not shown) as previously described. The sample anions are thus separated in the analytical column 8 according to methods known by those skilled in the art.

The analytical column effluent is then routed to suppressor column 12, which is preferably constructed as illustrated in FIG. 1 and which is packed with cation exchange packing material (for anion analysis). The cation exchange packing material preferably comprises exchangeable hydronium ion; (not shown) as previously described. The organic anion eluant is converted to its organic acid form by ion exchange with the cation exchange packing material in suppressor column 12. Similarly, the sample anions are converted to their highly conductive acid form by ion exchange with the cation exchange packing material in column 12.

Thus, two of the ion-exchange reactions that take place in the suppressor column 12 are:

1) Eluant:

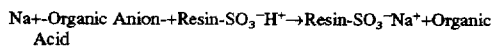

2) Analyte:

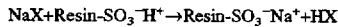

where X=anions (Cl, $NO_2$, Br, etc.)

The suppressor column effluent is then routed through a hydrophobic suppressor 50b, which is packed with organic or inorganic reversed-phase packing material (not shown), and preferably with organic reversed phase packing material. The preferred reversed-phase packing material comprises polystyrene divinyl benzene copolymer. The organic acid eluant is adsorbed on the packing material in column 50b and retained. The inorganic sample anions (which are in their acid form) are not adsorbed by the hydrophobic suppressor 50b and are routed to conductivity detector 18 as high conductivity acids in a stream of water where they are detected. This device significantly increases signal to noise ratios, just as (other suppressors do, but may be used with a much wider range of eluants, columns and methods.

Figure 12B:
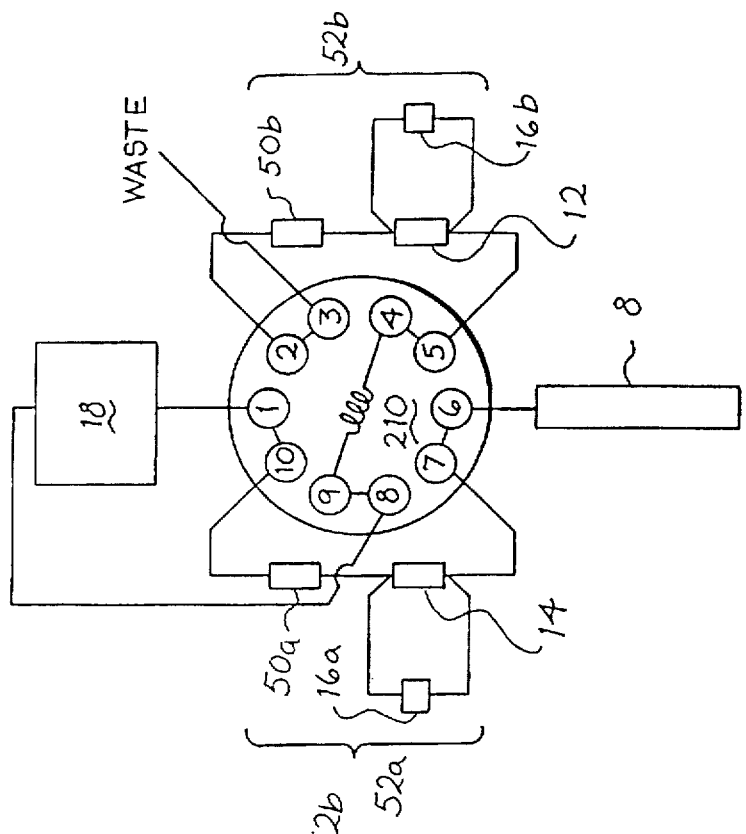
FIGS. 12A and 12B are schematic views of a chromatography apparatus where the column of FIG. 1 is used in a hydrophobic suppressor unit.
Figure 12A:
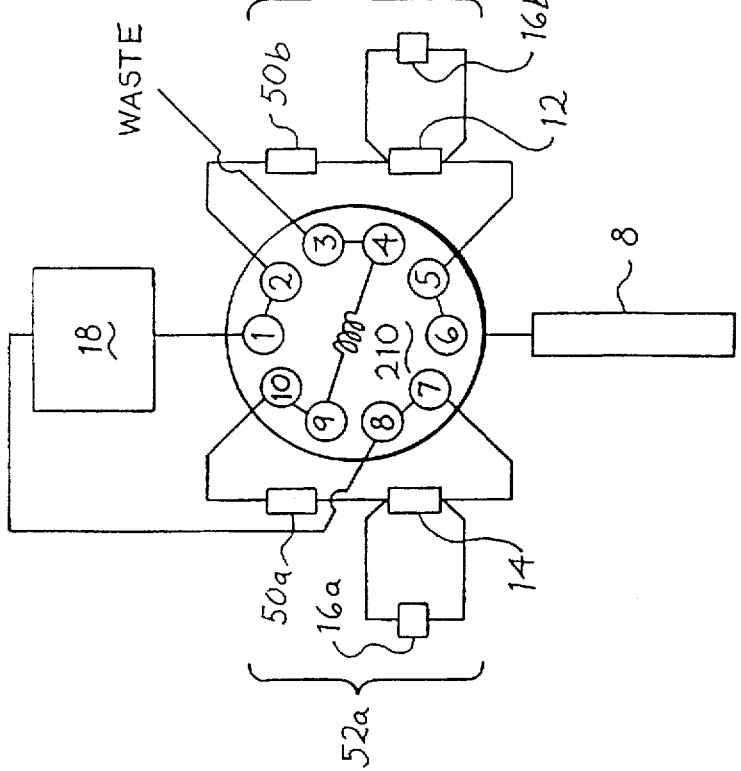

The combination of the column of the present invention with a hydrophobic suppressor can be used to construct continuously-regenerable hydrophobic suppressor units 52a and 52b as illustrated in FIGS. 12A and 12B.

The system depicted in FIGS. 12A and 12B will function properly until either the cation exchange packing material in columns 12 or 14 become exhausted (converted to the sodium form) or until the capacity of the hydrophobic suppressors 50a or 50b to adsorb the eluant organic acid is exceeded. The relative bed sizes for the suppressor columns 12 and 14 and the hydrophobic suppressors 50a and 50b are preferably chosen so that the capacity of the suppressor columns 12 and 14 are exceeded before that of the hydrophobic suppressors 50a or 50b.

With reference to FIGS. 12A and 12B, two such hydrophobic suppressor units 52a and 52b, respectively, may be used in any of the valve arrangements previously described. Before the first hydrophobic suppressor unit 52a is exhausted, the valve 10 is switched (see FIG. 12B) and the detector effluent is re-routed through the exhausted hydrophobic suppressor unit 52b. The detector effluent contains the sample inorganic anions in their acid form and water. The water in the detector effluent is used to feed electrolysis for regenerating the exhausted hydrophobic suppressor unit 52b. This is accomplished as follows.

The detector effluent is routed to suppressor column 12 and power source 16b is turned on to generate an electric current sufficient for the electrolysis of water across the exhausted cation exchange packing material in column 12. The anode is located at the upstream end of the suppressor column 12. Hydronium ions are thus generated at the upstream side of suppressor column 12 as previously described. The hydronium ions are routed through column 12 and displace the sample and eluant counterions on the exhausted cation exchange packing material thereby regenerating the packing material. The hydroxide ions generated at the cathode, which is located at the downstream end of the suppressor column 12, combine with the released sample and eluant counterions from the column 12 to form their hydroxides.

These hydroxides are then routed through the hydrophobic suppressor 50b before going to waste. It is well known that organic acids in their ionized state are very poorly adsorbed by hydrophobic packing materials. Thus, as the hydroxides are routed through the hydrophobic suppressor 50b, the strongly adsorbed organic acids are converted back to their weakly adsorbed ionized salts causing them to desorb from the hydrophobic suppressor 50b. The hydrophobic suppressor effluent is then routed to waste through 10-port valve switch 210. In this way, both the hydrophobic suppressor 50b and the suppressor column 12 are simultaneously regenerated.

A similar configuration can be envisioned for hydrophobic suppression in cation analysis, except that the polarity of the suppressor columns 12 and 14 are reversed, the suppressor columns are packed with anion exchange packing material comprising exchangeable hydroxide ions. The same hydrophobic suppressor packing material as previously described for anion analysis, however, may be used for cation analysis as well.

6. Other Applications

As those skilled in the art will readily appreciate based on the foregoing disclosure, the columns and methods of the present invention can be used in a variety of other applications as well. For example, the column illustrated in FIG. 1 can be used as a sample pretreatment device to reduce the pH of basic samples or to increase pH of acidic samples. The columns of the present invention can be packed with cation exchange packing material in the hydrogen form as previously described and can be used to reduce sample pH, removing hydroxide or carbonate. When the cation exchange packing is exhausted, it can be electrochemically regenerated as previously described. Conversely, the columns of the present invention can be packed with anion exchange packing material as previously described to increase sample pH or remove hydrogen ions. When the anion exchange packing material is exhausted, it can be electrochemically regenerated as previously described.

The column illustrated in FIG. 1 can also be used for other post column reactions that are pH-dependent. For example, the columns of the present invention can also be used to regenerate solid phase reagent (SPR) suppressors. In SPR, an aqueous suspension of submicron size resin is added post-column to the eluant stream to chemically suppress the eluant. U.S. Pat. No. 5,149,661 provides a detailed discussion of SPR, the disclosure of which is fully incorporated by reference herein. By using the column and methods of the present invention to perform electrolysis on the detector effluent, the released hydrogen or hydroxide ions can electrochemically regenerate the reagent and it can be recirculated on-line.

The column illustrated in FIG. 1 may also be adapted as a preconcentration device for ion analysis. The column may be packed with any of the chromatography packing materials previously described. Samples containing components with a strong attraction to the chosen packing may be routed through the column where they will be retained on the packing contained therein. Thereafter, water may be routed through the column and power supplied to elute the sample as previously described. Very large volumes of dilute samples may be passed through the column. The retained sample mass may be electrochemically eluted in a much smaller volume and at a much higher concentration greatly aiding subsequent separation and/or detection by, for example, chromatography, atomic adsorption, ICP, or mass spectrometry.

As those skilled in the art will appreciate based on the foregoing disclosure, the apparatuses and methods of the present invention are based on electrochemically modifying the mobile phase (e.g., the eluant) to modify the retention of a compound or species on the stationary phase (e.g., the chromatography material). Thus, the inventions and apparatuses of the present invention are not limited to the use of water-containing eluants. Indeed, any eluant that can be electrochemically modified is contemplated for use in the methods and apparatuses of the present invention. For instance, eluants containing non-aqueous species are also suitable for use in the present invention. Suitable non-aqueous species include alkyl, aromatic and olefinic alcohols, halogens, and thiols; aromatics in the presence of a nucleophile; and organic acids, sulfuric and nitric acids (non-aqueous). However, where such non-aqueous species are used as the eluant, catalytic electrodes may be required. For example, where methyl alcohol (e.g., methanol) is used as the eluant, the following reactions take place at catalytically active rheuthenium cyanide electrodes:

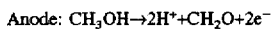
Anode: $CH_3OH \rightarrow 2H^+ + CH_2O + 2e^-$

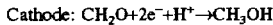
Cathode: $CH_2O + 2e^- + H^+ \rightarrow CH_3OH$

Thus, as those skilled in the art will readily appreciate, by electrochemically modifying the mobile phase (e.g., the eluant), the environment within the effluent flow channel may be modified which thereby modifies the retention or affinity of the compound or species retained on the chromatography material in the effluent flow channel.

Finally, the methods and columns of the present invention have other, far-reaching applications outside of the chromatography field. For example, the methods and apparatuses of the present invention can be applied to achieve a self-regenerating home water-softening system. For example, suitable chromatography packing materials (such as the ion-exchange packing materials previously described) can be used to remove cations (e.g. hardness) from the water. Once the chromatography packing material is exhausted, it can be regenerated as previously described by the electrolysis of water.

In order to illustrate certain embodiments of the present invention, the following examples are provided. However, the examples should not be construed as to limiting the present invention, the scope of which is defined by the appended claims and their equivalents.

EXAMPLE 1

Figure 13:
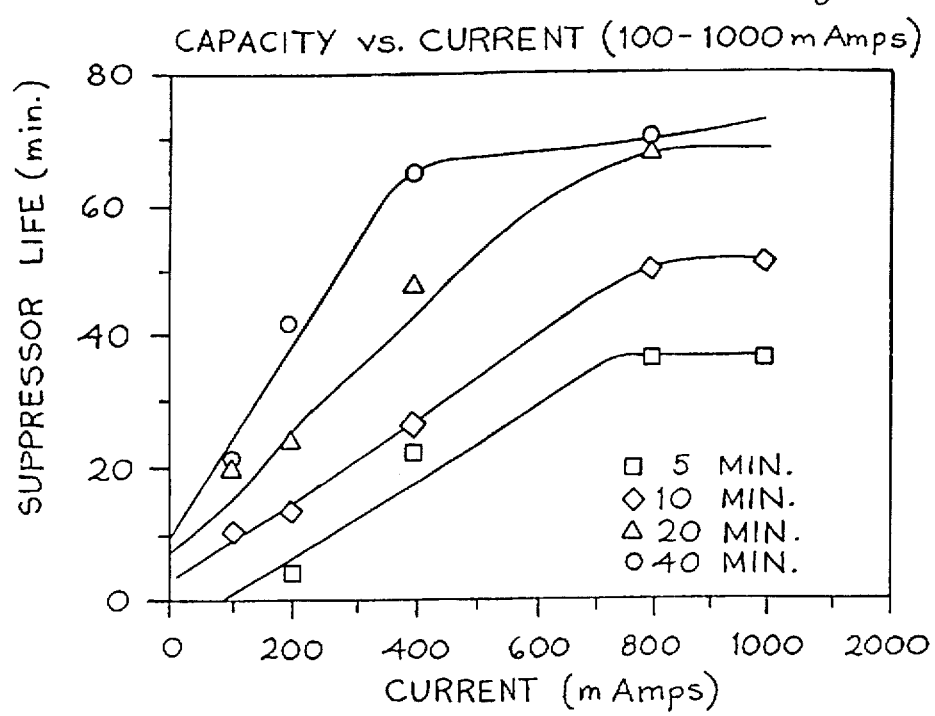
FIG. 13 is a graph illustrating the suppression capacity of a column according to one embodiment of the present invention.
Figure 14:
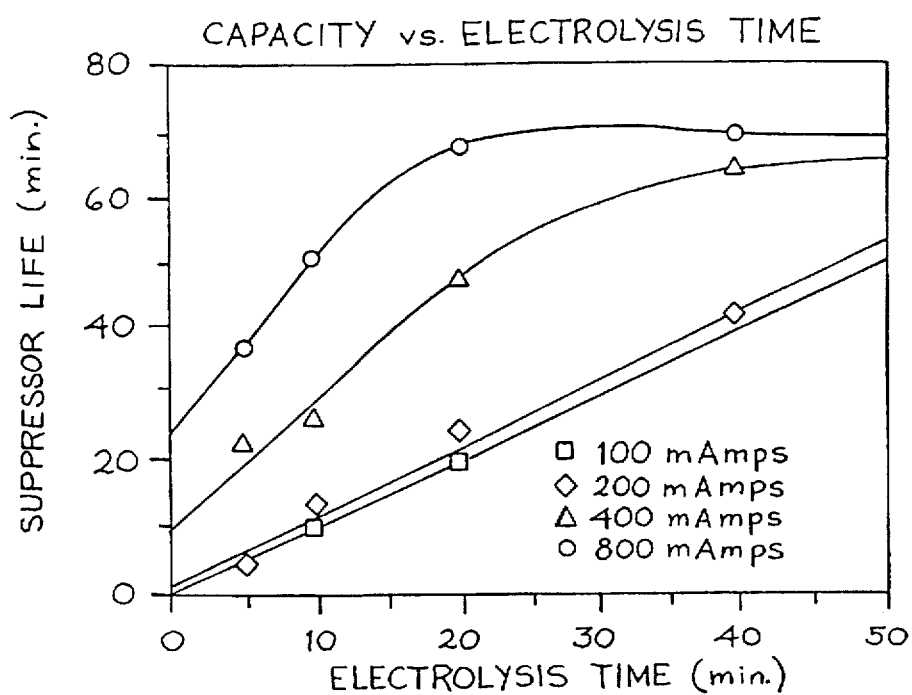
FIG. 14 is a graph illustrating the suppression life of a column according to one embodiment of the present invention.

Relationship between current, regeneration or electrolysis time, and suppressor capacity or lifetime FIG. 13 shows the relationship between the suppressor capacity of a column according to the present invention and the applied current during regeneration. The voltage applied across the column during the electrolysis is between 3–5 V. FIG. 14 shows the relationship between suppressor capacity and electrolysis regeneration time. These results show that there is a linear relationship between electrolysis time, current, and suppressor capacity. Several of the curves in FIGS. 13 and 14 have slopes greater than 1 demons rating that the column of the present invention can be electrochemically regenerated in less time than it takes to exhaust during use. This is required for cycling between two columns to work.

EXAMPLE 2

Reproducibility of the Regeneration Process

When three electrolysis regenerations were performed repeatedly on the same column (10 minute electrolysis at 400 mAmps (¾" diameter opening)), the following results were obtained:

| Trial # | Suppressor Capacity (min) |
|---|---|
| 1 | 129 |
| 2 | 130 |
| 3 | 132 |

These results indicate that the regeneration process is consistent and reproducible.

EXAMPLE 3

Chromatography

Figure 15:
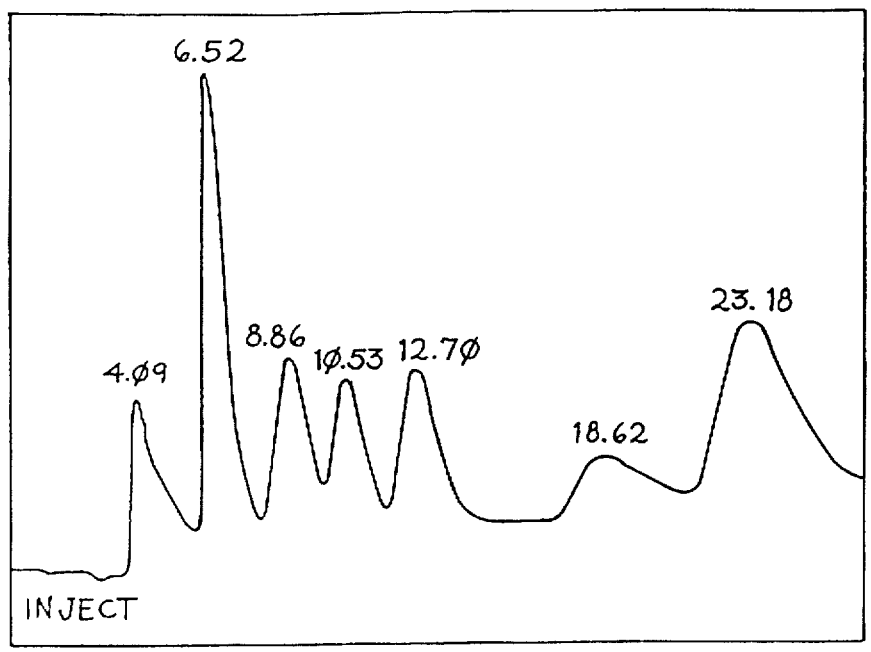
FIG. 15 is a chromatogram of a sample containing ions using a column according to one embodiment of the present invention.
Figure 16:
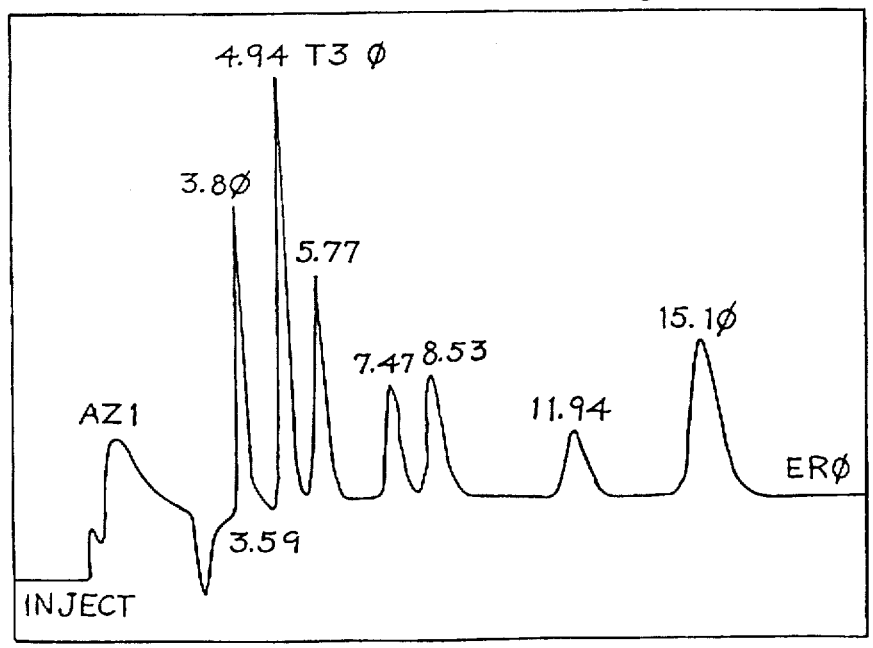
FIG. 16 is a chromatogram of a sample containing ions using a column according to one embodiment of the present invention.

FIG. 15 shows a chromatogram of anions obtained using the column of the present invention as a suppressor with 1" diameter column packed with sulfonic-acid functionalized polystyrene-divinyl benzene cation exchange packing material. The peaks are broad due to band broadening, resulting in loss of chromatographic efficiency. The band broadening is due to the large void volume in the suppressor column. FIG. 16 shows a chromatogram of anions obtained using 0.75 cm diameter cell packed with the same cation-exchange packing material. By reducing the bed diameter, band broadening is reduced.

EXAMPLE 4

Electroelution Ion Chromatography (Anion analysis)

The following materials and conditions were used in this example:

Column: 6 mm×7.5 mm packed with anion-exchange functionalized organic particles (trimethylammonium functionalized divinylbenzene polymer)

Eluant: Deionized water

Flow rate: 1.0 mL/min.

Detector: 350 conductivity detector

Sample: Anion (fluoride, chloride)

Electrolysis: Constant Voltage

Results

Figure 17:
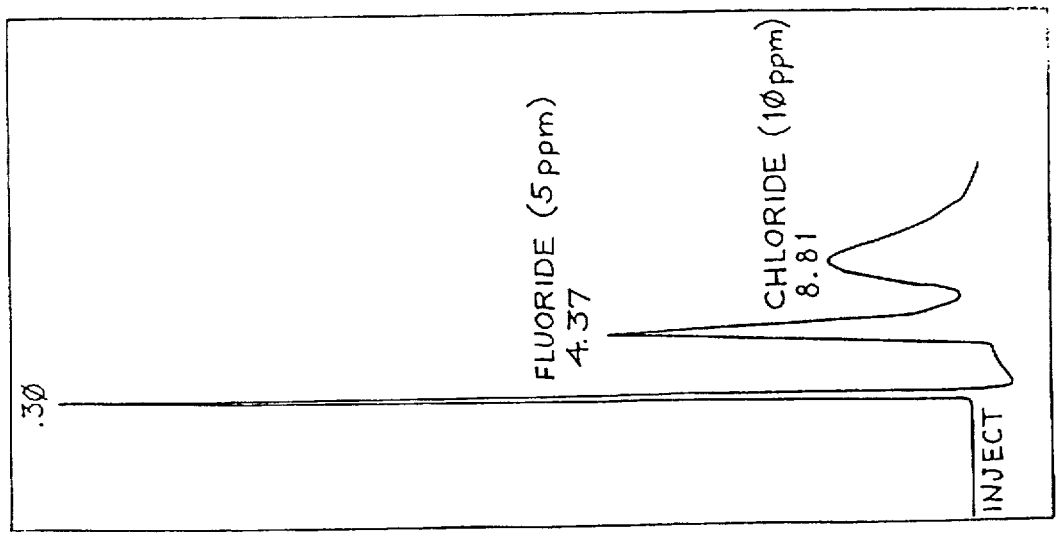
FIG. 17 is a chromatogram of a sample containing ions using a column according to one embodiment of the present invention.

FIG. 17 shows a separation of fluoride and chloride obtained on this column. The electrolysis was conducted at 28 V. A backpressure regulator of 100 psi was installed at the detector outlet to reduce bubble formation from the generation of $O_2(g)$ and $H_2(g)$ during the electrolysis.

EXAMPLE 5

Cation Analysis Using Electrochemically Regenerated Suppressor Column

The following materials and conditions were used:

Suppressor: Suppressor A—7.5 mm ID×0.9 mm thick Suppressor B—10 mm ID×0.31" thick Amount of packing: Packed with 0.40 grams anion exchange resin in hydroxide form (trimethylammonium functionalized polystyrene-divinylbenzene polymer) (Suppressors installed in 10-port Micro-Electric Actuator)

Column: ALLTECH Universal Cation Column (polybutadiene-maleic acid coated silica particles)

Eluant: 3 mM Methane Sulfonic Acid

Flow rate: 1.0 mL/min.

Detector: 350 Conductivity Detector

Figure 18:
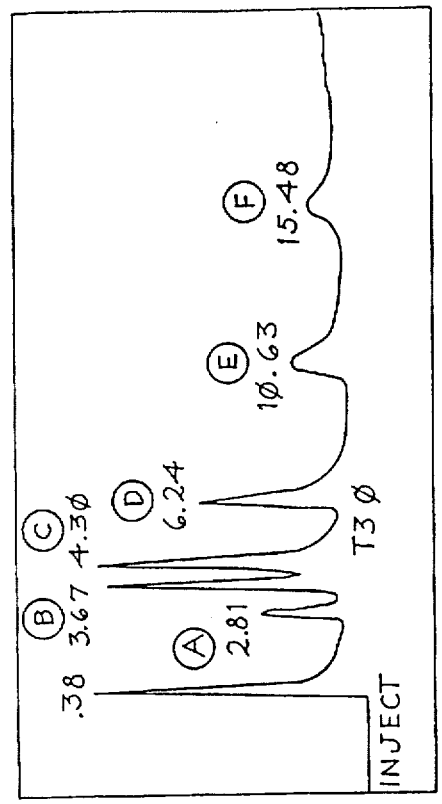
FIG. 18 is a chromatogram of a sample containing ions using a column according to one embodiment of the present invention.

Sample: injections (A) lithium, (B) sodium, (C) ammonium, (D) potassium, (E) magnesium, (F) calcium, 50 µL injection Electrolysis: Constant current at 79 mAmps Results FIG. 18 shows a separation of cations obtained using a column according to the present invention as a suppressor for cation analysis.

EXAMPLE 6

Electroelution Ion Chromatography (Cation Analysis) With Water Containing Eluant The following materials and conditions were used:

Column: 30 mm×4.6 mm packed with ALLTECH Universal Cation Column (polybutadiene-maleic acid coated silica particles)

Eluant: Deionized water containing 0.1 mm methane sulfonic acid

Flowrate: 1.0 mL/min

Detector: model 350 conductivity detector

Sample: lithium, sodium, ammonium, potassium

Results

Deionized water was used as the eluant originally. Since a much longer column (30 mm-very high resistant) was used, the power supply (this power supply has 36V upper limit) was not able to generate current for electrolysis. No elution of cations was observed. A small amount of methane sulfonic acid was added to the water to reduce the resistance of the water eluant.

Figure 19:
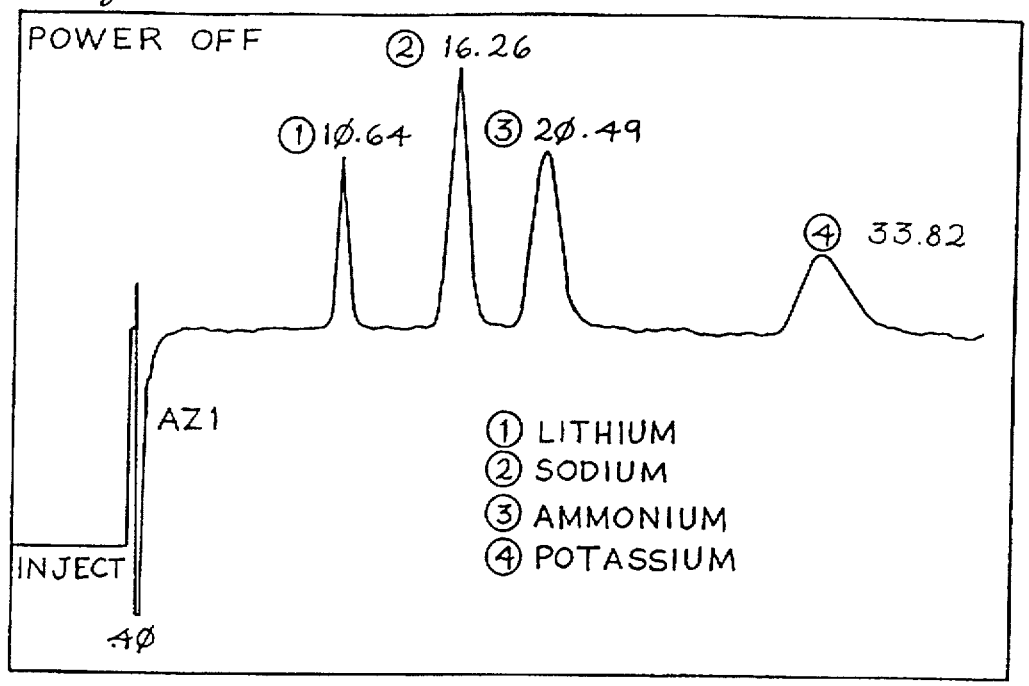
FIG. 19 is a chromatogram of a sample containing ions using a column according to one embodiment of the present invention.
Figure 20:
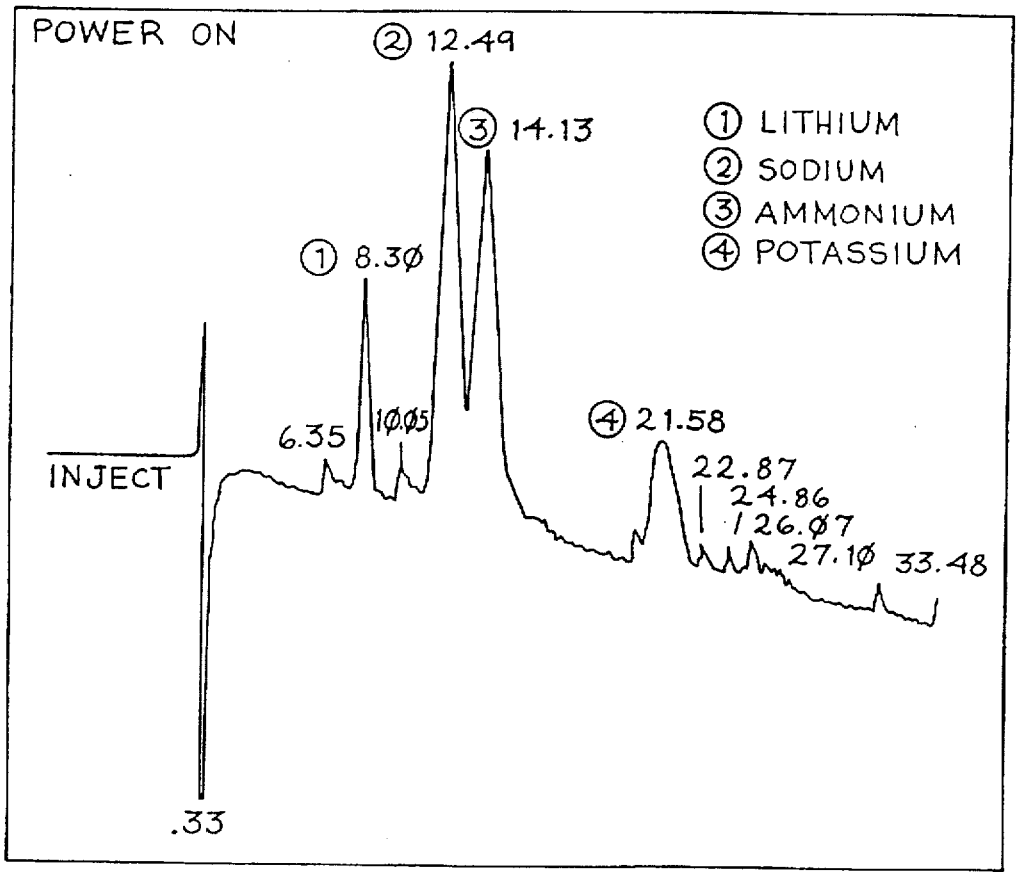
FIG. 20 is a chromatogram of a sample containing ions using a column according to one embodiment of the present invention.

FIG. 19 shows the separation of the 4 cations with just the 0.1 mm methane sulfonic acid and water as the eluant (power supply was turned off). FIG. 20 shows the same separation with the power on. The peaks are eluted at much shorter time in FIG. 20. Thus, when the concentration of the hydronium ions is increased by generating an electric current in the column, the sample cations are eluted faster. The electrolysis was conducted at 28V. As depicted in FIG. 20, some baseline noise was detected in the analysis, which was caused by the bubbles formed during electrolysis of water. A backpressure regulator was not used in this analysis.

EXAMPLE 7

Gradient Electroelution Ion Chromatography (Anion Analysis)

The following materials and conditions were used in this example:

Column: 6 mm×7.5 mm column packed with anion exchange functionalized organic particles (trimethylammonium functionalized divinylbenzene polymer)

Eluant: Deionized water

Flowrate: 1.0 mL/min

Detector: model 350 conductivity detector

Sample: fluoride (5 ppm), chloride (10 ppm), nitrate (10 ppm); 50 µm injection

Results

Figure 22:
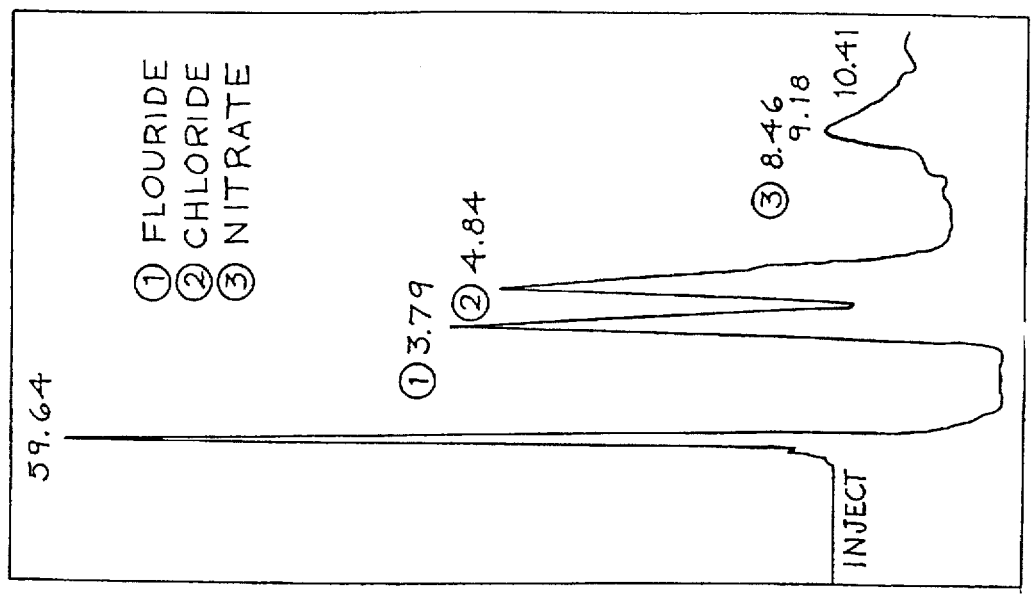
FIG. 22 is a chromatogram of a sample containing ions using a column according to one embodiment of the present invention.
Figure 21:
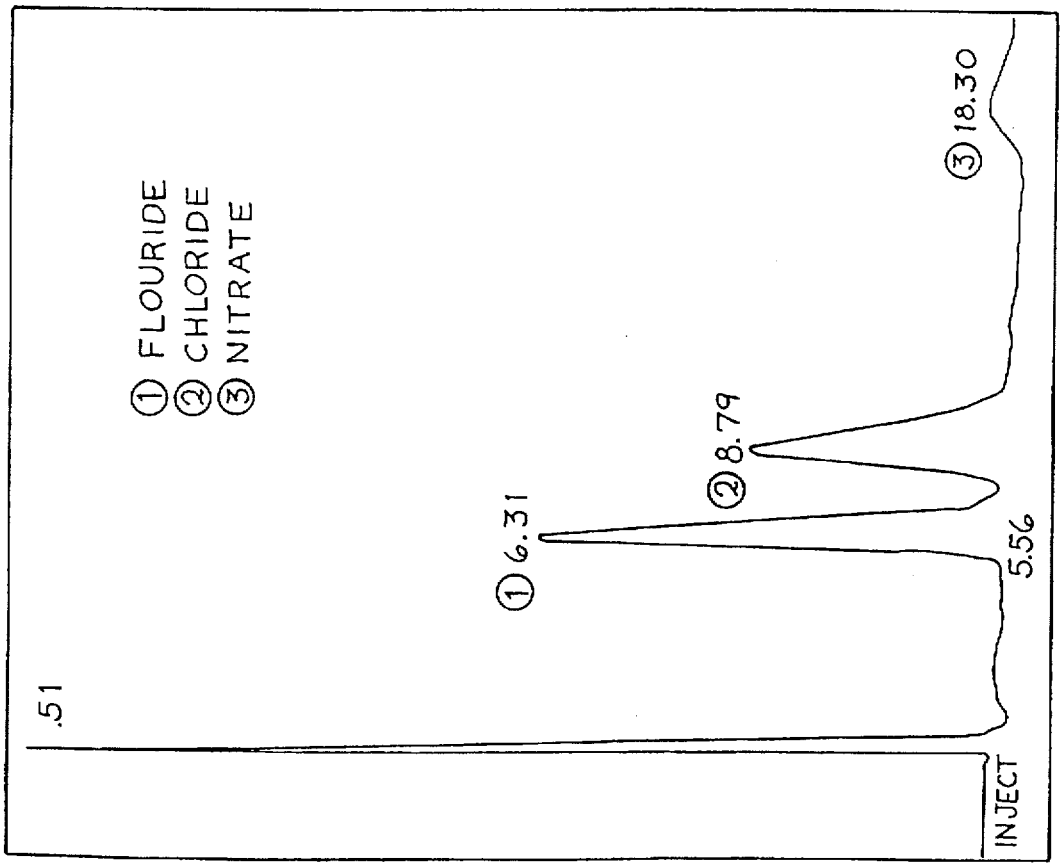
FIG. 21 is a chromatogram of a sample containing ions using a column according to one embodiment of the present invention.

FIG. 21 shows a separation of fluoride, chloride, and nitrate obtained on this column with constant current electrolysis at 10 mAmp. The retention time for fluoride, chloride, and nitrate are 6.31, 8.79, and 18.3 minutes, respectively. FIG. 22 shows the separation of the same components on this column with constant current electrolysis at 16 mAmp. By increasing the current, the retention time for all anions is reduced. These results indicate that the amount of hydroxide ions produced during electrolysis is proportional to the amount of current used. By varying the electric current during the separation, the concentration of the eluant may be varied, thereby generating a gradient.

We claim:

1. A method of electroelution chromatography for detecting species in a sample, the method comprising:
  a) providing a stationary phase wherein at least a portion of the stationary phase is positioned between a first electrode and a second electrode;
  b) flowing the species to be separated through the stationary phase where the species are retained thereon;
  c) providing water;
  d) conducting electrolysis of the water to generate electrolysis ions comprising hydronium ions and hydroxide ions;
  e) eluting the retained species by flowing the electrolysis ions selected from the group consisting of hydroxide ions, hydronium ions or mixtures thereof through the stationary phase; and
  f) subsequently flowing the eluted species to a detector for detection.

2. The method of claim 1 wherein the species to be separated comprises anions; the first electrode is positioned upstream in the direction of fluid flow from the second electrode; the first electrode is the cathode; the second electrode is the anode; and the stationary phase comprises anion exchange packing material.

3. The method of claim 1 wherein the species to be separated comprises cations; the first electrode is positioned upstream in the direction of fluid flow from the second electrode; the first electrode is the anode, the second electrode is the cathode; and the stationary phase comprises cation exchange packing material.

4. The method of claim 1 wherein the species to be separated comprises protein.

5. A method of electroelution chromatography for detecting ions in a sample comprising:
  a) providing water;
  b) providing chromatography material comprising exchangeable ions of the sample ions;
  c) flowing the sample ions through the chromatography material thereby retaining the sample ions on the chromatography material;
  d) generating additional exchangeable ions of the sample ions by the electrolysis of water;
  e) eluting the retained sample ions by flowing the exchangeable ions from the electrolysis through the chromatography material; and
  f) subsequently flowing the sample ions to a detector for detection.

6. The method of claim 5 wherein the water further comprises eluant.

7. The method of claim 6 wherein the sample ions comprise anions and cations.

8. The method of claim 6 wherein the sample ions comprise anions.

9. The method of claim 6 wherein the sample ions comprise cations.

10. The method of claim 6 wherein the sample ions comprise anions and a portion of the hydroxide ions and hydronium ions from the electrolysis of the eluant are combined to form water and a portion of the hydronium ions from the electrolysis are combined with the sample anions to form the acid of the sample anions before flowing the sample anions to the detector.

11. The method of claim 10 wherein the acid of the sample anions is flowed from the detector to an ion exchange bed comprising exchangeable hydroxide ions where the acid of the sample anions is converted to water by ion exchange.

12. The method of claim 11 wherein the water recited in step (a) of claim 5 comprises the water generated in the ion exchange bed.

13. The method of claim 6 wherein the sample ions comprise cations and a portion of the hydroxide ions and hydronium ions from the electrolysis of the eluant are combined to form water and a portion of the hydroxide ions from the electrolysis are combined with the sample cations to form the base of the sample cations before flowing the sample cations to the detector.

14. The method of claim 13 wherein the base of the sample cations is flowed from the detector to an ion exchange bed comprising exchangeable hydronium ions where the base of the sample cations are converted to water by ion exchange.

15. The method of claim 14 wherein the water recited in step (a) of claim 5 comprises the water generated in the ion exchange bed.

16. A method for generating a high purity eluant for detecting sample ions comprising:

providing water;

providing sample ions;

providing eluant generating chromatography material comprising counter-ions of the sample ions;

generating electrolysis ions by the electrolysis of water wherein the electrolysis ions are selected from the group consisting of hydronium ions and hydroxide ions; and wherein either the hydronium ions or hyroxide ions are exchangeable with the sample counter-ions in the eluant generating chromatography material;

flowing the exchangeable electrolysis ions through the eluant generating chromatography material so that the exchangeable electrolysis ions replace the sample counter ions in the chromatography material;

combining the sample counter-ions with the other of the electrolysis ions which are not exchangeable with the sample counter-ions to form an eluant;

flowing the sample ions and eluant to a chromatography column for separating the sample ions; and flowing the separated sample ions to a detector for detection.

17. The method of claim 16 wherein the eluant is suppressed and the sample ions are converted to either their acid or base form prior to detection, by flowing the separated sample ions and eluant through suppressor chromatography material comprising suppressor ions selected from the group consisting of hydronium ions and hydroxide ions such that the suppressor ions are replaced on the suppressor chromatography material by the sample counter-ions of the eluant and some of the suppressor ions combine with the electrolysis ions of the eluant to form water and other of the suppressor ions combine with the sample ions to form either the acid or base of the sample ions prior to detection of the sample ions.

18. The method of claim 17 wherein after the detection the sample ions in either their base or acid form are flowed through post-detector chromatography material comprising exchangeable ions of the sample ions thereby converting the acid or base form of the sample ions to water by ion exchange.

19. The method of claim 18 wherein the suppressor chromatography material is regenerated by generating electrolysis ions selected from the group consisting of hydronium ions and hydroxide ions by performing electrolysis of the water from the post-detector chromatography material and flowing the electrolysis ions that are exchangeable with the retained sample counter-ions through the suppressor chromatography material thereby releasing the retained sample counter-ions by ion exchange.

20. The method of claim 19 wherein the eluant generating chromatography material is regenerated by flowing the released sample counter-ions from the suppressor chromatography material to the eluant generating chromatography material thereby releasing the retained electrolysis ions on the eluant generating chromatography material by ion exchange with the sample counter-ions.

21. The method of claim 20 wherein the sample ions comprise anions; the sample counter-ions comprise cations; the exchangeable electrolysis ions flowed through the eluant generating chromatography material comprise hydronium ions; the sample counter-ions are combined with the electrolysis ions comprising hydroxide ions to form the eluant; the sample anions are converted to their acid form by combining with electrolysis ions comprising hydronium ions in the suppressor chromatography material; the post-detector chromatography material comprises hydroxide ions; and the electrolysis ions that regenerate the suppressor chromatography material comprise hydronium ions.

22. The method of claim 21 wherein the sample counter-ions comprise sodium ions.

23. The method of claim 20 wherein the sample ions comprise cations, the sample counter-ions comprise anions; the exchangeable electrolysis ions flowed through the eluant generating chromatography material comprise hydroxide ions; the sample counter-ions are combined with the electrolysis ions comprising hydronium ions to form the eluant; the sample cations are converted to their base form by combining with electrolysis ions comprising hydroxide ions in the suppressor chromatography material; the post-detector chromatography material comprises hydronium ions; and the electrolysis ions that regenerate the suppressor chromatography material comprise hydroxide ions.

* * * * *

UNITED STATES PATENT AND TRADEMARK OFFICE
CERTIFICATE OF CORRECTION

PATENT NO. : 5,759,405
DATED : June 2, 1998
INVENTOR(S) : Anderson, Jr. et al.

It is certified that error appears in the above-identified patent and that said Letters Patent is hereby corrected as shown below:

On the Title Page

On page 2, column 1, after line 3, under "OTHER PUBLICATIONS", please insert a blank line.

On page 2, column 1, line 6, under "OTHER PUBLICATIONS", please change "no" to --No--.

On page 2, column 2, line 12, please change "*Chromatorgraphy,*" to --*Chromatography,*--.

On page 2, column 2, line 22, please change "(SRS)"No" to --(SRS)" No--.

In claim 16, lines 10-11, please change "hyroxide" to --hydroxide--.

Signed and Sealed this

Ninth Day of January, 2001

Attest:

Attesting Officer

Q. TODD DICKINSON

Commissioner of Patents and Trademarks